US011234953B2

(12) United States Patent
Veech et al.

(10) Patent No.: US 11,234,953 B2
(45) Date of Patent: *Feb. 1, 2022

(54) KETONE BODIES TO PROTECT TISSUES FROM DAMAGE BY IONIZING RADIATION

(71) Applicants: TDELTAS LIMITED, Thame (GB); THE UNITED STATES OF AMERICA, AS REPRESENTED BY THE SECRETARY, DEPARTMENT OF HEALTH AND HUMAN SERVICES, Bethesda, MD (US)

(72) Inventors: Richard Lewis Veech, Rockville, MD (US); Kieran Clarke, Oxford (GB)

(73) Assignees: TDELTAS LIMITED, Thame (GB); THE UNITED STATES OF AMERICA, AS REPRESENTED BY THE SECRETARY, DEPARTMENT OF HEALTH AND HUMAN SERVICES, Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/594,431

(22) Filed: Oct. 7, 2019

(65) Prior Publication Data

US 2020/0215016 A1 Jul. 9, 2020

Related U.S. Application Data

(63) Continuation of application No. 15/403,982, filed on Jan. 11, 2017, now Pat. No. 10,478,415, which is a continuation of application No. 14/440,634, filed as application No. PCT/US2013/068545 on Nov. 5, 2013, now Pat. No. 9,579,302.

(60) Provisional application No. 61/722,630, filed on Nov. 5, 2012.

(51) Int. Cl.
A61K 31/32 (2006.01)
A61K 31/22 (2006.01)

(52) U.S. Cl.
CPC .................................. A61K 31/22 (2013.01)

(58) Field of Classification Search
CPC ..................................................... A61K 31/22
USPC ....................................................... 514/546
See application file for complete search history.

(56) References Cited

U.S. PATENT DOCUMENTS

| | | | |
|---|---|---|---|
| 3,984,566 A | 10/1976 | Van Scott et al. | |
| 4,380,549 A | 4/1983 | Van Scott et al. | |
| 5,112,865 A | 5/1992 | Nichels et al. | |
| 5,281,691 A | 1/1994 | Hubbs et al. | |
| 5,468,507 A | 11/1995 | Czap | |
| 5,654,266 A | 8/1997 | Chen et al. | |
| 5,665,831 A | 9/1997 | Neuenschwander et al. | |
| 5,693,850 A | 12/1997 | Birkhahn et al. | |
| 6,126,953 A | 10/2000 | Costa et al. | |
| 6,136,862 A | 10/2000 | Hiraide et al. | |
| 6,207,856 B1 | 3/2001 | Veech | |
| 6,268,167 B1 | 7/2001 | Wild et al. | |
| 6,316,038 B1 | 11/2001 | Veech | |
| 6,323,237 B1 | 11/2001 | Veech | |
| 6,380,244 B2 | 4/2002 | Martin et al. | |
| 6,544,960 B1 | 4/2003 | Eldred et al. | |
| 6,939,570 B1 | 9/2005 | Snow et al. | |
| 7,351,736 B2 | 4/2008 | Veech | |
| 7,947,736 B2 | 5/2011 | Gross | |
| 8,101,653 B2 | 1/2012 | Veech | |
| 8,642,654 B2 | 2/2014 | Clarke | |
| 9,034,613 B2 | 5/2015 | Robertson et al. | |
| 9,211,275 B2 | 12/2015 | Clarke et al. | |
| 9,579,302 B2 * | 2/2017 | Veech .................... | A61K 31/22 |
| 10,478,415 B2 * | 11/2019 | Veech .................... | A61P 43/00 |
| 10,821,062 B2 * | 11/2020 | Clarke ................... | A61Q 17/04 |
| 2001/0014696 A1 | 8/2001 | Veech et al. | |
| 2001/0041741 A1 | 11/2001 | Sole et al. | |
| 2001/0047008 A1 | 11/2001 | Baraldi | |
| 2002/0006959 A1 | 1/2002 | Henderson | |
| 2002/0013339 A1 | 1/2002 | Martin et al. | |
| 2002/0035231 A1 | 3/2002 | Whitehouse et al. | |
| 2003/0022937 A1 | 1/2003 | Veech et al. | |
| 2004/0006263 A1 | 1/2004 | Anderson et al. | |
| 2004/0063661 A1 | 4/2004 | Linnane | |
| 2004/0171671 A1 | 9/2004 | Veech | |
| 2004/0266872 A1 | 12/2004 | Veech et al. | |
| 2005/0129783 A1 | 6/2005 | McCleary et al. | |
| 2005/0165318 A1 | 7/2005 | Brodnick et al. | |
| 2005/0181275 A1 | 8/2005 | Jang | |
| 2005/0182235 A1 | 8/2005 | Zhong et al. | |
| 2006/0078596 A1 | 4/2006 | Clarke et al. | |
| 2006/0280721 A1 * | 12/2006 | Veech .................... | C07H 13/04 424/78.37 |

(Continued)

FOREIGN PATENT DOCUMENTS

| | | |
|---|---|---|
| CA | 1330307 C | 6/1994 |
| CA | 2173270 A | 10/1996 |

(Continued)

OTHER PUBLICATIONS

Abdelwahab et al. "The ketogenic diet is an effective adjuvant to radiation therapy for the treatment of malignant glioma.", PLOS ONE 2012, vol. 7, No. 5, May 1, 2012 (May 1, 2012), p. e36197, ISSN: 1932-6203.*

(Continued)

*Primary Examiner* — Nizal S Chandrakumar
(74) *Attorney, Agent, or Firm* — Brian C. Trinque; Lathrop GPM LLP

(57) ABSTRACT

Described herein is the surprising discovery that ketone bodies protect cell and tissues from ionizing radiation. Based on this finding, methods of protecting animal tissue and cells from damage caused by radiation exposure are disclosed which include, contacting the tissue with a therapeutically effective amount of an agent including at least one ketone ester, thereby protecting the tissue from radiation damage. Ketone esters can be used to minimize, reduce and/or prevent tissue damage following intentional and accidental radiation exposure, as well as increasing the therapeutic efficacy of radiation therapies by protecting non-target tissue from incidental radiation damage.

26 Claims, 5 Drawing Sheets

(56) References Cited

U.S. PATENT DOCUMENTS

| | | |
|---|---|---|
| 2007/0179197 A1 | 8/2007 | Henderson et al. |
| 2008/0287372 A1 | 11/2008 | Henderson et al. |
| 2009/0197952 A1 | 8/2009 | Hashim et al. |
| 2009/0253781 A1 | 10/2009 | Veech |
| 2010/0298294 A1 | 11/2010 | Clarke et al. |
| 2011/0237666 A1 | 9/2011 | Clarke et al. |
| 2012/0064611 A1 | 3/2012 | Robertson et al. |
| 2012/0071548 A1 | 3/2012 | Veech |
| 2012/0213835 A1 | 8/2012 | Neas et al. |
| 2013/0102663 A1 | 4/2013 | Clarke et al. |
| 2014/0194509 A1 | 7/2014 | Clarke et al. |
| 2014/0308719 A1 | 10/2014 | Clarke et al. |
| 2015/0065571 A1 | 3/2015 | Clarke et al. |
| 2015/0164855 A1 | 6/2015 | Clarke et al. |
| 2015/0250755 A1 | 9/2015 | Veech et al. |
| 2016/0030314 A1 | 2/2016 | Clarke et al. |
| 2016/0193173 A1 | 7/2016 | Clarke et al. |

FOREIGN PATENT DOCUMENTS

| | | |
|---|---|---|
| CN | 1483355 A | 9/2002 |
| CN | 1552315 A | 12/2004 |
| DE | 20205184 U | 12/2002 |
| EP | 0 266 217 A2 | 5/1988 |
| EP | 0 537 113 A1 | 4/1993 |
| EP | 0 552 896 A1 | 7/1993 |
| EP | 0 721 740 A1 | 7/1996 |
| EP | 1 568 780 A1 | 8/2005 |
| EP | 1 809 235 B1 | 7/2007 |
| EP | 2 875 812 A1 | 5/2015 |
| GB | 1524611 A | 9/1978 |
| GB | 0312603.4 | 6/2003 |
| GB | 0313760.1 | 6/2003 |
| GB | 2511941 A | 9/2014 |
| JP | S54-138126 A | 10/1979 |
| JP | S63-112998 A | 5/1988 |
| JP | H01-095730 A | 4/1989 |
| JP | H01-160917 A | 6/1989 |
| JP | H03-083950 A | 4/1991 |
| JP | H04-112825 A | 4/1992 |
| JP | H07-076513 A | 3/1995 |
| JP | H08-191664 A | 7/1996 |
| JP | H10-175855 A | 6/1998 |
| JP | H10-265378 A | 10/1998 |
| JP | H10-313819 A | 12/1998 |
| JP | 2001-515510 A | 9/2001 |
| JP | 2005-247821 A | 9/2005 |
| JP | 2008-513017 A | 5/2008 |
| JP | 2008-127369 A | 6/2008 |
| JP | 2008-263825 A | 11/2008 |
| JP | 2009-532496 A | 9/2009 |
| JP | 2012-500264 A | 1/2012 |
| SU | 507322 A | 3/1976 |
| WO | 1987/003806 A1 | 7/1987 |
| WO | 1995/009144 A1 | 4/1995 |
| WO | 1998/041200 A1 | 9/1998 |
| WO | 1998/041201 A1 | 9/1998 |
| WO | 1999/024451 A2 | 5/1999 |
| WO | 2000/004895 A1 | 2/2000 |
| WO | 2000/015216 A1 | 3/2000 |
| WO | 2001/013877 A1 | 3/2001 |
| WO | 2001/051645 A1 | 7/2001 |
| WO | 2002/006368 A2 | 1/2002 |
| WO | 2003/012417 A2 | 2/2003 |
| WO | 2003/056319 A2 | 7/2003 |
| WO | 2003/097860 A1 | 11/2003 |
| WO | 2004/105742 A1 | 12/2004 |
| WO | 2004/108740 A1 | 12/2004 |
| WO | 2006/020137 A2 | 2/2006 |
| WO | 2006/031941 A2 | 3/2006 |
| WO | 2006/061624 A1 | 6/2006 |
| WO | 2006/070337 A2 | 7/2006 |
| WO | 2007/001883 A2 | 1/2007 |
| WO | 2007/063037 A2 | 6/2007 |
| WO | 2007/115282 A2 | 10/2007 |
| WO | 2007/115934 A1 | 10/2007 |
| WO | 2008/074473 A2 | 6/2008 |
| WO | 2008/119032 A1 | 10/2008 |
| WO | 2008/140828 A1 | 11/2008 |
| WO | 2009/023357 A2 | 2/2009 |
| WO | 2009/089144 A1 | 7/2009 |
| WO | 2010/021766 A1 | 2/2010 |
| WO | 2010/120300 A1 | 10/2010 |
| WO | 2011/101171 A1 | 8/2011 |
| WO | 2011/121540 A1 | 10/2011 |
| WO | 2012/113415 A1 | 8/2012 |
| WO | 2013/150153 A1 | 10/2013 |
| WO | 2014/071389 A1 | 5/2014 |
| WO | 2014/139599 A1 | 9/2014 |
| WO | 2014/153416 A1 | 9/2014 |

OTHER PUBLICATIONS

Database Medline [Online] US National Library of Medicine (NLM), Bethesda, MD, US; Jan. 1993 (Jan. 1993), Kulinskii V I et al.: "[The radioprotective effect of GABA-tropic substances, gamma-hydroxybutyrate and piracetam].", Database accession No. NLM8469734.*

Database Medline [Online] US National Library of Medicine (NLM), Bethesda, MD, US; 1988, Davey P et al.: "Radioprotection of rat subependymal plate with 4-OH sodium butyrate.", Database accession No. NLM3352771.*

Abdelwahab et al. (2012) "The Ketogenic Diet Is an Effective Adjuvant to Radiation Therapy for the Treatment of Malignant Glioma," PLOS ONE. 7(5):E36197. pp. 1-7.

Boyarinov et al. (1984) "Effect of Sodium hydroxybutyrate on myocardial high-energy phosphates, function, and ultrastructure after blood loss," Byulleten Eksperimental'noi Biologii i Meditsiny. 97(3):289-292.

Buteau (2009) "Obviousness of Enantiomers over Prior Art Racemates," The Journal of High Technology Law. L22. pp. 42-49.

Clark et al. (2005) "Dilated Cardiomyopathy and Acute Liver Injury Associated with Combined Use of Ephedra, yHydroxybutyrate, and Anabolic Steroids" Pharmacotherapy. 25(5):756-761.

Davey et al. (1988) "Radioprotection of rat subependymal plate with 4-0H sodium butyrate," NCI Monogr. (6):231-234.

Desrochers et al. (1992) "Metabolism of R and S-1 ,3-butanediol in perfused livers from meal-fed and starved rats," Biochem. J. 285:647-653.

Desrochers et al. (1995) "Metabolism of (R,S)-1 ,3-butanediol acetoacetate esters, potential parenteral and enteral nutrients in conscious pigs," Am. J. Physiol. 268:E660-667.

Desrochers et al. (1995) "R, S-1,3-butanediol acetoacetate esters, potential alternates to lipid emulsions for total parenteral nutrition," Journal of Nutritional Biochemistry. 6(2):111-118.

Eagles et al. (1997) "The effects of combined treatment with Beta-1-selective receptor antagonists and lipid-lowering drugs on fat metabolism and measures of fatigue during moderate intensity exercise: a placebo-controlled study in healthy subjects," Brit. J. Clinical Pharmacol. 43:291-300.

Edegger et al. (2006) "Regia- and Stereoselective Reduction of Diketones and Oxidation of Dials by Biocatalytic Hydrogen Transfer," Eur. J. Org. Chem. 2006(8):1904-1909.

Felig et al. (1971) "Amino acid metabolism in exercising man." J. Clin. Invest. 50(12):2703-2714.

Frayn (2003) In; Metabolic Regulation: A Human Perspective. 2nd Ed. Blackwell Science, pp. 94-96.

Goldbort et al. (1976) "Butanediols: Selection, open field activity, and NAD reduction by liver extracts in inbred mouse strains," Pharmacology Biochemistry and Behaviour. 5(3):263-268.

Kalaitzakis et al. (2005) "Highly Stereoselective Reductions of a-Aikyl-1 ,3-diketones and a-Aikyi-Jl-keto Esters Catalyzed by Isolated NADPH-Dependent Ketoreductases," Org. Lett. 7(22):4799-4801.

Kashiwaya et al. (2013) "A ketone ester diet exhibits anxiolytic and cognition-sparing properties, and lessens amyloid and tau pathologies in a mouse model of Alzheimer's disease," Neurobiology of Aging. 34(6):1530-1539.

(56) References Cited

OTHER PUBLICATIONS

Kohut et al. (1995) "Effects of decresased free fatty acids on fatigue during exercise with carbohydrate feedings," Medicine and Science in Sports & Exercise. 27(5 Suppl):S102.
Kulinskii et al. (1993) "The radioprotective effect of GABA-tropic substances, gamma-hydroxybutyrate and piracetam," Radiobiologiia. 33(1):133-136.—English Abstract Only.
Larios et al. (2004) "Synthesis of flavor and fragrance esters using Candida antarctica lipase," Appl. Microbiol. Biotechnol. 65:373-376.
Mahley et al. (2006) "Drug Therapy of Dyslipidemia," In; Goodman & Gilman's The Pharmacological Basis of Therapeutics. 11th Ed. Eds.: Brunton et al. McGraw-Hill. New York, New York. pp. 948-953.
Mori et al. (1987) "New synthesis of both enantiomers of grandisol, the boll weevil pheromon," Tetrahedron. 43(10):2229-2239.
Nair et al. (1988) "Effect of beta-hydroxybutyrate on whole-body leucine kinetics and fractional mixed skeletal muscle protein synthesis in humans," J. Clin. Invest. 82(1):198-205.
Neubauer et al. (1997) "Myocardial Phosphocreatine-to-ATP Ratio is a predictor of mortality in patients with dilated cardiomyopathy," Circulation. 96:2190-2196.
Ostrovskaya et al. (1981) "Effect of prolonged administration of sodium hydroxybutyrate on the working capacity and muscle tissue in rats," Farmakologiya I Toksikologiya. 44(5):534-539.—Only English Abstract Provided.
Puchowicz et al. (2000) "Dog model of therapeutic ketosis induced by oral administration of R,S-1,3-butanediol diacetoacetate," J. Nutr. Biochem. 11:281-287.
Rossi et al. (2000) "Suppression of feed intake after parenteral administration of D-beta-hydroxybutyrate in pygmy goats," J. Vet. Med. A. 47:9-16.
Shaw et al. (1984) "Influence of beta-hydroxybutyrate infusion on glucose and free fatty acid metabolism in docs," Am. J. Phys. 247:E756-764.
Sherwin et al. (1975) "Effect of ketone infusions on amino acid and nitrogen metabolism in man" J. Clin. Invest. 55(6) 1382-1390.
Simons et al. (1982) "Long term treatment with Slow Release Oxprenolol Alone, or in Combination with other Drugs: Effects on Blood Pressure, Lipoproteins and Exercise Performance," Aust. N. Z. J. Med. 12:612-616.
Smith et al. (1975) "Initial effect of injury on ketone bodies and other blood metabolites," Lancet. 1:7897. pp. 1-3.
Tobin et al., "Effect Of 1,3-Butanediol and Propionic Acid on Blood Ketones, lipids d Metal Ions in Rats", Journal of Nutrition, vol. 102, No. 8, 1972, pp. 1001-1008.
Turner et al. "Glycemic control with diet, sulfonylurea, metformin, or insulin in patients with type 2 diabetes mellitus: progressive requirement for multiple therapies (UKPDS 49)." Jama 281.21 (1999): 2005-2012.
Wu et al. (1987) "Ketone bodies inhibit leucine degradationin chick skeletal muscle," International J. of Biochem. 19(10):937-943.
Zhu et al. (2006) "A recombinant ketoreductase tool-box. Assessing the substrate selectivity and stereoselectivity toward the reduction of JI-ketoesters," Tetrahedron. 62:901-905.
Examination Report corresponding to Great Britain Patent Application No. 1404400.2, dated Aug. 18, 2014.
International Preliminary Report on Patentability corresponding to International Patent Application No. PCT/US2009/030095 dated Jul. 6, 2010.
International Preliminary Report on Patentability corresponding to International Patent Application No. PCT/US2009/040773, dated Oct. 18, 2011.
International Search Report with Written Opinion corresponding to International Patent Application No. PCT/EP2011/000833, dated Jun. 22, 2011.
International Search Report with Written Opinion corresponding to International Patent Application No. PCT/EP2013/057250, dated Jun. 11, 2013.
International Search Report with Written Opinion corresponding to International Patent Application No. PCT/GB2004/002286, dated Oct. 11, 2004.
International Search Report with Written Opinion corresponding to International Patent Application No. PCT/US2004/018016, dated Apr. 15, 2005.
International Search Report with Written Opinion corresponding to International Patent Application No. PCT/US2009/040766, dated Aug. 6, 2009.
International Search Report with Written Opinion corresponding to International Patent Application No. PCT/US2009/040773, dated Feb. 22, 2010.
International Search Report with Written Opinion corresponding to International Patent Application No. PCT/US2013/068545, dated Jan. 20, 2014.
Search and Examination Report corresponding to Great Britain Patent Application No. 1404400.2, dated Mar. 26, 2014.
Search and Examination Report corresponding to Great Britain Patent Application No. 1404577.7, dated Oct. 23, 2014.
Search and Examination Report corresponding to Great Britain Patent Application No. 1414016.4, dated Aug. 29, 2014.
Search Report corresponding to Great Britain Patent Application No. 1002983.3, dated Jun. 10, 2010.
Search Report corresponding to Great Britain Patent Application No. 1304467.2, dated Aug. 23, 2013.
Search Report corresponding to Great Britain Patent Application No. 1314127.0. dated Jan. 31, 2014.
Supplementary European Search Report and Written Opinion corresponding to European Patent Application No. 09701051.6, dated Jan. 19, 2011.
U.S. Appl. No. 13/580,602, filed Jan. 4, 2013, 2013/0102663 Apr. 25, 2013, U.S. Pat. No. 10,660,958 May 26, 2020, Kieran Clarke.
U.S. Appl. No. 11/287,803 / 2006/0078596, filed Nov. 28, 2005 / Apr. 13, 2006, Kieran Clarke.
U.S. Appl. No. 12/811,648, filed Jul. 2, 2010, 2010/0298294 Nov. 25, 2010, U.S. Pat. No. 9,211,275 Dec. 15, 2015, Kieran Clarke.
U.S. Appl. No. 14/931,265, filed Nov. 3, 2015, 2016/0193173 Jul. 7, 2016, U.S. Pat. No. 10,154,982 Dec. 18, 2018, Kieran Clarke.
U.S. Appl. No. 13/264,533, filed Oct. 14, 2011, 2012/0064611 Mar. 15, 2012, U.S. Pat. No. 9,034,613 May 19, 2015, Jeremy Robertson.
U.S. Appl. No. 14/231,713 / 2014/0308719, filed Mar. 14, 2014 / Oct. 16, 2014, Kieran Clarke.
U.S. Appl. No. 14/453,999 / 2015/0065571, filed Aug. 7, 2014 / Mar. 5, 2015, Kieran Clarke.
U.S. Appl. No. 14/390,495 / 2015/0164855, filed Oct. 3, 2014 / Jun. 18, 2015, Kieran Clarke.
U.S. Appl. No. 14/440,634, filed May 5, 2015, 2015/0250755 Sep. 10, 2015, U.S. Pat. No. 9,579,302 Feb. 28, 2017, Richard L. Veech.
U.S. Appl. No. 15/403,982, filed Jan. 11, 2017, 2017/0196827 Jul. 13, 2017, U.S. Pat. No. 10,478,415 Nov. 19, 2019, Richard L. Veech.
U.S. Appl. No. 14/774,856, filed Sep. 11, 2015, 2016/0030314 Feb. 4, 2016, U.S. Pat. No. 10,821,062 Nov. 3, 2020, Kieran Clarke.
U.S. Appl. No. 13/031,006, filed Feb. 18, 2011, 2011/0237666 Sep. 29, 2011, U.S. Pat. No. 8,642,654 Feb. 4, 2014, Kieran Clarke.
U.S. Appl. No. 14/101,834, filed Dec. 10, 2013, 2014/0194509 Jul. 10, 2014, U.S. Pat. No. 10,051,880 Aug. 21, 2018, Kieran Clarke.
Baron et al. (1991) "Mechanism of insulin resistance in insulin-dependent diabetes mellitus: a major role for reduced skeletal muscle blood flow," J. Clin. Endocrinol. Metab. 73(3):637-643.
Boehm et al. (2001) "Increased uncoupling proteins and decreased efficiency in the palmitate-perfused hyperthyroid rat heart," Am. J. Physiol. Heart Circ. Physiol. 2809(3):H977-H983.
Casey et al. (1990) In; Advanced Practical Organic Chemistry. Blackie. Glasgow and London, U.K. pp. 158-160.
Chatham et al. (1999) "Preferential inhibition of lactate oxidation relative to glucose oxidation in the rat heart following diabetes," Cardiovasc Res. 43(1):96-106.
Chatham et al. (2002) "Cardiac carbohydrate metabolism in Zucker diabetic fatty rats," Cardiovasc Res. 55(1):104-112.
Chen et al. (Nov. 13, 2016) "β-hydroxybutyrate protects from alcoholic hepatitis via a GPR109a-C/EBPβ dependent pathway," AASLD LiverLearning. Abstract No. 1629. Accessible on the Internet at URL: http://liverlearning.aasld.org/aasld/2016/thelivermeeting/144521/yonglin.chen.b-hydroxybutyrate.protects.from.alcoholic.hepatitis.via.a.html. [Last Accessed Apr. 5, 2017].

(56) References Cited

OTHER PUBLICATIONS

Cole et al. (2011) "A high fat diet increases mitochondrial fatty acid oxidation and uncoupling to decrease efficiency in rat heart," Basic Res. Cardiol. 106:447-457.

Cox et al. (Oct. 29, 2014) "Acute nutritional ketosis: implications for exercise performance and metabolism," Extrem. Physiol Med. 3:17. pp. 1-9.

Demir et al. (2001) "Serum HbA1c levels and exercise capacity in diabetic patients," Jpn. Heart J. 42(5):607-616.

Estacio et al. (1998) "The association between diabetic complications and exercise capacity in NIDDM patients," Diabetes Care. 21(2):291-295.

Gangemi "Enhancing Athletic Performance by Predicting Fatigue and Preventing Muscle Failure," Accessible on the Internet at URL: http://www.drgangemi.com/wp-content/uploads/2011/01/GANGEMI-PREDICTING-FATIGUE-AND-MUSCLE-FAILURE.pdf. [Last Accessed Sep. 20, 2011].

Iozzo et al. (2002) "Mismatch between insulin-mediated glucose uptake and blood flow in the heart of patients with Type II diabetes," Diabetologia. 45(10):1404-1409.

Kemper et al. (Oct. 26, 2015) "An Ester of β-Hydroxybutyrate Regulates Cholesterol Biosynthesis in Rats and a Cholesterol Biomarker in Human," Lipids. 50(12):1185-1193.

Knowler et al. (2002) "Reduction in the incidence of type 2 diabetes with lifestyle intervention or metformin," New Engl. J. Med. 346:393-403.

Komiyama et al. (2000) "Near-infrared spectroscopy grades the severity of intermittent claudication in diabetes more accurately than ankle pressure measurement," British Journal of Surgery. 87(4):459-466.

Komiyama et al. (2004) "Effects of a 4-week 70% high carbohydrate / 15% low fat diet on glucose tolerance and on lipid profiles," Diabetes Res. Clin. Pract. 64(1):11-18.

Kwiterovich et al. (2003) "Effect of a high-fat ketogenic diet on plasma levels of lipids, lipoproteins, and apolipoproteins in children," JAMA. 290(7):912-920.

Lanni et al. (2002) "De Novo Expression of Uncoupling Protein 3 is Associated to Enhanced Mitochondrial Thioesterase-1 Expression and Fatty Acid Metabolism in Liver of Fenofibrate-treated Rats," FEBS Letters. 525:7-12.

Libby et al. (2002) "Diabetic macrovascular disease. The glucose paradox?" Circulation. 106(22):2760-2763.

Lodi et al. (1999) "Reduced cytosolic acidification during exercise suggests defective glycolytic activity in skeletal muscle of patients with Becker muscular dystrophy. An in vivo 31P magnetic resonance spectroscopy study," Brain. 121(1):121-130.

Madsen et al. (1999) "Near-infrared oximetry of the brain," Prog. Neurobiol. 58(6):541-560.

Mahler et al. (1999) "Type 2 diabetes mellitus: update on diagnosis, pathophysiology, and treatment," J. Clin. Endocrinol. Metab. 84(4):1165-1171.

Meyer et al. (1997) "Myocardial blood flow and glucose metabolism in diabetes mellitus," Am. J. Cardiol. 80(3,Suppl 1):94A-101A.

Mori et al. (1984) "Synthesis of the Propionates of (2R, 8R)- and (2S, 8R)-8-methyl-2-decanol, the pheromone of the Western corn rootworm, employing chiral compounds of microbial origin as starting material," Tetrahedron. 40(2):299-303.

Murray et al. (2004) "Uncoupling Proteins in Human Heart," Lancet. 364:1786-1788.

Murray et al. (2005) "Plasma Free Fatty Acids and Peroxisome Proliferator-Activated Receptor a in the Control of Myocardial Uncoupling Protein Levels," Diabetes. 54(12):3496-3502.

Newsholme et al. (1986) In; Biochemistry for the Medical Sciences. John Wiley & Sons. Chichester, U.K. pp. 324-331.

O'Neill et al. (1994) "A simple enantioselective synthesis of γ-valerolactone," Tetrahedron Asymmetry. 5(1):117-118.

Paolisso et al. (1999) "Prognostic importance of insulin-mediated glucose uptake in aged patients with congestive heart failure secondary to mitral and/or aortic valve disease," Am. J. Cardiol. 83(9):1338-1344.

Perez-Jimenez et al. (2001) "A Mediterranean and a high-carbohydrate diet improve glucose metabolism in healthy young persons," Diabetologia. 44(11):2038-2043.

Richieri et al. (1995) "Unbound free fatty acid levels in human serum," Journal of Lipid Research. 36(2):229-240.

Rodrigues et al. (1998) "Metabolic disturbances in diabetic cardiomyopathy," Molecular and Cellular Biochemistry. 180(1-2):53-57.

Salehizadeh et al. (2004) "Production of polyhydroxyalkanoates by mixed culture: recent trends and biotechnological importance," Biotechnol. Advances. 22:261-279.

Sato et al. (1995) "Insulin, ketone bodies, and mitochondrial energy transduction," FASEB J. 9(8):651-658.

Scheuermann-Freestone et al. (2003) "Abnormal cardiac and skeletal muscle energy metabolism in patients with type 2 diabetes," Circulation. 107(24):3040-3046.

Seebach et al. (1993) "Direct Degradation of the Biopolymer Poly[(R)-3-Hydroxybutyric Acid] to (R)-3-Hydroxybutanoic Acid and its Methyl Ester," Organic Syntheses, Coll. vol. 9., p. 483 (1998); vol. 71., p. 39. (1993).

Sidell et al. (2002) "Thiazolidinedione treatment normalizes insulin resistance and ischemic injury in the Zucker fatty rat heart," Diabetes. 51(4):1110-1117.

Silva et al. (2004) "Poly-3-hydroxybutyrate (P3HB) production by bacteria from xylose, glucose and sugarcane bagasse hydrolysate," J. Ind. Microbiol. Biotechnol. 31:245-254.

Smith et al. (2002) "Magnetic Resonance Spectroscopy in Medicine: Clinical Impact," Progress in Nuclear Magnetic Resonance Spectroscopy. 40:1-34.

Stanley et al. (1997) "Regulation of energy substrate metabolism in the diabetic heart," Cardiovasc. Res. 34(1):25-33.

Taegtmeyer et al. (2002) "Adaptation and maladaptation of the heart in diabetes: Part I. General concepts," Circulation. 105(14):1727-1733.

Tinnikov et al. (1999) "Colorimetric micro-determination of free fatty acids in plasma using microplate readers," Clinica Chemica Acta. 281(1-2):159-162.

Toubro et al. (1998) "Twenty-four-hour respiratory quotient: the role of diet and familial resemblance," J. Clin. Endocrinol. Metab. 83(8):2758-2764.

Tunaru et al. (2003) "PUMA-G and HM74 are receptors for nicotinic acid and mediate its anti-lipolytic effect," Nat. Med. 9(3):352-355.

Zange et al. (2002) "Creatine Supplementation Results in Elevated Phosphocreatine/Adenosine Triphosphate (ATP) Ratios in the Calf Muscle of Athletes But Not in Patients with Myopathies," Annals of Neurology. 53(1):126-127.

International Search Report with Written Opinion corresponding to International Patent Application No. PCT/EP2013/069189, dated Aug. 12, 2014.

International Search Report with Written Opinion corresponding to International Patent Application No. PCT/EP2014/055158, dated Jun. 25, 2014.

International Search Report with Written Opinion corresponding to International Patent Application No. PCT/EP2014/067027, dated Oct. 30, 2014.

International Search Report with Written Opinion corresponding to International Patent Application No. PCT/US2009/030095, dated Feb. 23, 2009.

Strahlentherapie, el al. (1977) "Zeitschrift fur Radiologie and Onkologie," National Library, Mar. 16, 1977 53(2), 117-123.

Chen et al. (Feb. 2016) "Beta-hydroxybutyrate reduces alcoholic steatohepatits (ASH) via activation of the GPR 109A Receptor," Proceedings of the American Society for Hematology, 2016. Abstract No. 26. pp. 143-144.

Farmer et al. (1973) "Radioprotective Thiazolidines from beta-keto esters," J. Med. Chem. 16(4):411-413.

\* cited by examiner

| Dose (Gy) | Gamma Radiation | | | | Gamma Radiation + Ketone | | | |
|---|---|---|---|---|---|---|---|---|
| | Percent Aberrant Cells | Fragments | Breaks | Rings + Dicentrics | Percent Aberrant Cells | Fragments | Breaks | Rings + Dicentrics |
| 0 | 0.66 ±0.055 | .007 ±0.0008 | .0019 ±.002 | .0006 ±— | 0.66 ±.07 | 0.007 ±.0009 | .0016 ±.0002 | 0.00±0.0 |
| 1 | 5.9 ± 0.61 | 0.11 ± 0.01 | 0.002 ± .0002 | 0.0013 ± .0002 | 3.1 ±.033 | 0.05 ±.006 | .0013±.0002 | 0.00±0.0 |
| 2 | 14.4 ± 1.22 | 0.3 ± 0.033 | 0.006 ±.0007 | 0.0129 ±.002 | 5.0±.052 | 0.118 ±.022 | .0018±.0002 | .003±.0004 |
| 3 | 28.5 ± 2.15 | 0.61 ±0.05 | 0.0105 ±.002 | 0.0279 ±.003 | 11.4 ±1.22 | 0.23 ±.028 | .0022±.0003 | .005±.0004 |
| 4 | 55.5 ± 5.58 | 1.1 ± 0.12 | 0.016 ±.002 | 0.0356 ±.004 | 19.5 ± 1.29 | 0.30 ±.031 | .0039±.0004 | .017±.002 |

KETONE BODIES TO PROTECT TISSUES FROM DAMAGE BY IONIZING RADIATION

CROSS REFERENCE TO RELATED APPLICATION

This application is a continuation of U.S. application Ser. No. 15/403,982, filed on Jan. 11, 2017, which is a continuation of U.S. application Ser. No. 14/440,634, filed on May 5, 2015, now U.S. Pat. No. 9,579,302, which is a 371 filing of International Application No. PCT/US2013/068545, filed Nov. 5, 2013, which claims the benefit of U.S. Provisional Patent Application No. 61/722,630, filed on Nov. 5, 2012, the contents of each of which are is-hereby incorporated by reference in their entirety.

FIELD OF THE DISCLOSURE

The present disclosure relates to compositions containing ketogenic compounds capable of reducing adverse effects of radiation exposure, as well as methods of using such ketogenic compounds to reduce or ameliorate or block one or more of the adverse effects of radiation exposure, such as reducing or meliorating or blocking ionizing radiation tissue damage. Particularly, the present disclosure relates to esters and oligomers of (R)-3-hydroxybutyrate that are capable of elevating blood levels of (R)-3-hydroxybutyrate and acetoactetate to sufficient levels to reduce, ameliorate or block said adverse effects, particularly cell death by apoptosis caused by ionizing radiation induced damage, e.g., of DNA and RNA.

BACKGROUND

Radiation has long been known to damage biological tissues and cells. Initial deposition of energy in irradiated cells occurs in the form of ionized and excited atoms or molecules distributed at random throughout the cells. The ionizations cause chemical changes in the exposed area, producing highly unstable charged or "ionized" molecules. These rapidly undergo chemical changes, producing free radicals that react with cellular components and lead to permanent damage.

As an immediate consequence of radiation damage, cells can undergo apoptosis, dying in interphase within a few hours of irradiation. Typical morphologic changes include loss of normal nuclear structure and degradation of DNA. DNA damage is important in triggering programmed cell death; membrane damage and signaling pathways are also thought to be involved.

A sufficiently high dose of radiation will inhibit mitosis. Inhibition of cellular proliferation is a mechanism by which radiation kills most cells. As radiation kills cells by inhibiting their ability to divide, its effects in living organisms occur primarily in tissues with high cell turnover or division rates, characterized by high proliferative activity.

The development of effective radioprotectant molecules is of great importance to populations potentially subjected to accidental, intentional or military exposure to radiation, including ionizing radiation.

SUMMARY OF THE DISCLOSURE

It has now been surprisingly determined that protection against radiation damage occurs if ketones ((R)-3-hydroxybutyrate or acetoactetate) or ketogenic substances are administered either before or after exposure to radiation. This effect is demonstrated herein using a particularly preferred (R)-3-hydroxybutyrate ester which can now be used as radioprotectant agent. Such agents find application in minimizing, reducing and/or preventing tissue damage following intentional and accidental radiation exposure, as well as increasing the therapeutic efficacy of radiation therapies by protecting non-target tissue from incidental radiation damage.

Provided herein are methods of protecting animal tissue from damage caused by radiation exposure, comprising contacting the tissue with a therapeutically effective amount of an agent including one or more ketone esters, thereby protecting the tissue from radiation damage.

In various embodiments, the disclosed methods include administering one or more (R)-3-hydroxybutyrate derivatives and compositions that include these derivatives. These compounds serve as precursors to ketone bodies, such as acetoacetate and (R)-3-hydroxybutyrate, and thus yield elevated circulating concentrations of ketone bodies when administered to a subject.

Examples of (R)-3-hydroxybutyrate derivatives suitable for use in the compositions and method include those taught by U.S. Patent Publication No. 2006/0280721 (Veech) which are esters of (R)-3-hydroxybutyrate and oligomers of (R)-3-hydroxybutyrate. Disclosed ester compounds include esters derived from alcohols, such as altrose, arabinose, dextrose, erythrose, fructose, galactose, glucose, glycerol, gulose, idose, lactose, lyxose, mannose, ribitol, ribose, ribulose, sucrose, talose, threose, xylitol, xylose, galactosamine, glucosamine, mannosamine, N-acetylglucosamine, mannitol, sorbitol, threitol, (S)-1,2-propanediol and (R)-1,3-butanediol Also described herein are uses of agents to reduce, prevent, or treat cell damage from radiation, where the agent is a ketone ester, such as one or more esters of (R)-3-hydroxybutyrate.

In its most preferred embodiment the present disclosure provides a method of providing a treatment for a subject that is suspected of having risk of exposure to non-therapeutic radiation comprising administering to that subject a protective amount of a ketone ester, more preferably that ester being an (R)-1,3-butanediol ester of (R)-3-hydroxybutyrate. Still more preferably the ester is a compound of formula I: 3-hydroxybutyl-(R)-3-hydroxybutyrate-monoester-taught by WO2010/120300 and WO2010/021766.

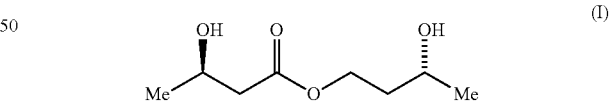
(I)

Such ester may be used in the form of an enantiomerically enriched composition as described in WO2010/021766 (which is hereby incorporated by reference in its entirety).

Preferably the treatment is by oral or parenteral administration of the ketogenic compound or compounds, optionally together with any combination therapy, such as to raise the blood ketone body concentration to between 0.1 mM and 20 mM, more preferably 0.2 mM and 10 mM, still more preferably to between 2 mM and 8 mM.

Suitable oral doses of the ketogenic compound will include between 5 grams to about 500 grams, For example the method may employ administering from about 70 milligrams to about 5 grams per kilogram of the subject's body weight, more preferably between 0.5 to 2 grams per kilogram, still more preferably 130 grams to about 170 grams per day to the subject.

The foregoing and other features and advantages of the disclosure will become more apparent from the following detailed description of several embodiments which proceeds with reference to the accompanying figures.

DETAILED DESCRIPTION OF SEVERAL EMBODIMENTS

I. Introduction

Figure 1:
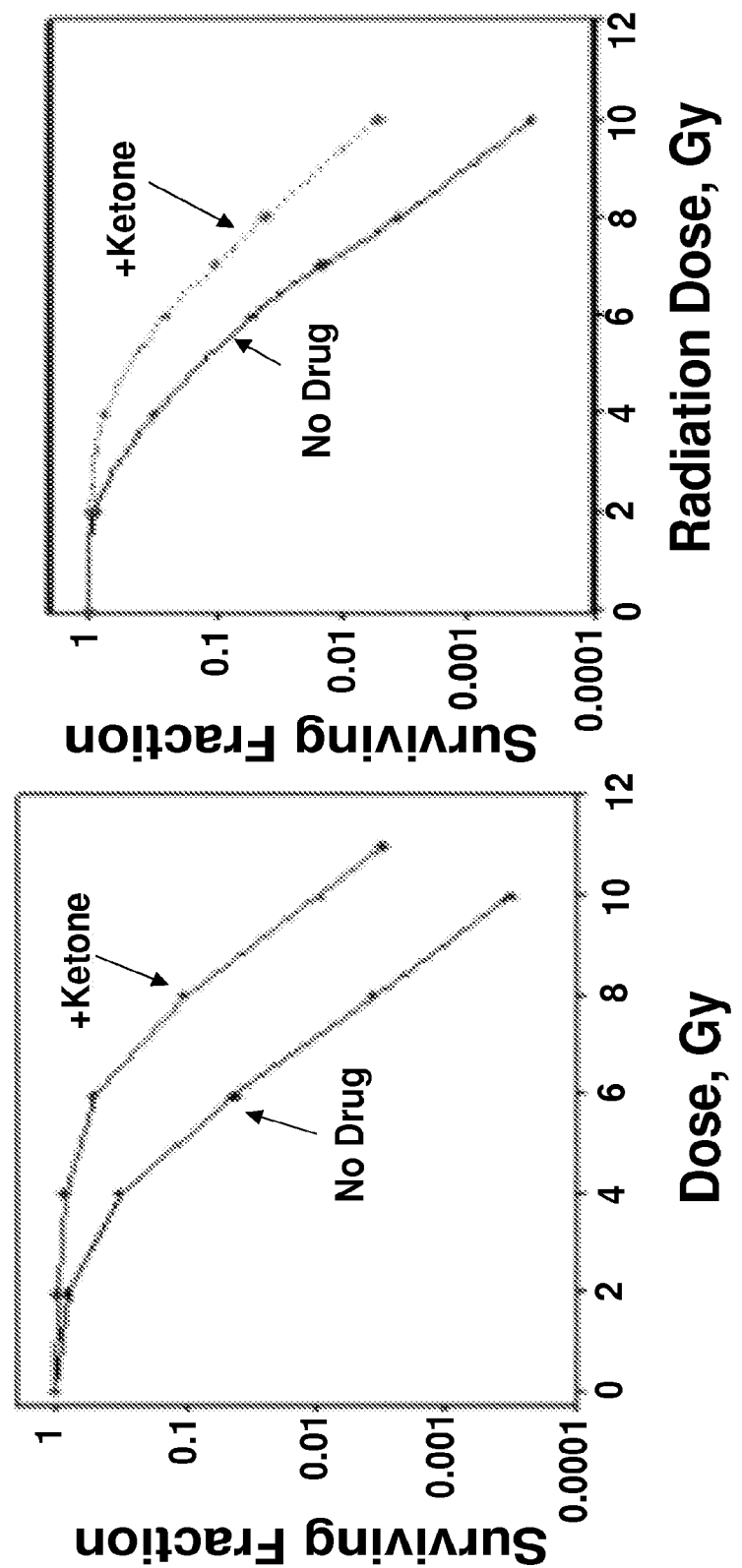
FIG. 1 is a pair of graphs illustrating cellular radioprotection by ketone esters. Human osteoblast cells (HOS) were treated with ketone esters either pre-(left panel) or post-(right panel) $^{60}$Co gamma radiation (0.6 Gy/min).

Tissue damage from radiation may result from the interaction between high energy radiation with water in a single electron oxidation of water to form the hydroxyl radical: $H_2O+hv \rightarrow HO^- +H^+ +e^-$. Alternatively, electrons can react with oxygen to form the superoxide radical: $O_2+e^- \rightarrow O_2^-$. Superoxide radicals and hydroxyl radicals can react with each other in a reaction catalyzed by the enzyme superoxide dismutase to form the non-toxic OH— ion and $O_2$, $HO^- + O_2^- \rightarrow OH^- +O_2$. Superoxide radicals can react with superoxide dismutase to form the less toxic $H_2O_2$:$O_2^- + O_2^- +2H^+ \rightarrow H_2O_2$:$O_2$. Hydrogen peroxide in turn can undergo a reaction catalyzed by catalase $2H_2O_2 \rightarrow O_2+2H_2O$. Alternatively, hydrogen peroxide can be destroyed by glutathione peroxidase: $2GSH+2H_2O_2 \rightarrow GSSG+2H_2O$. The terminal destructor of oxygen radicals is glutathione, which is present in most cells at concentrations of 5 mM and is responsible for the maintenance of the intracellular sulfhydryl groups in the reduced —SH form. Glutathione itself is maintained in the reduced state by a near-equilibrium reaction with the cytosolic [NADP+]/[NADPH] couple which is the most reduced redox pair in the cell with a very negative redox potential of 0.42V. The metabolism of ketone bodies reduces the NADP+/NADPH ratio.

In addition to being formed by ionizing radiation, free radicals can be formed by the mitochondrial electron transport system, the quantitatively most important reaction being the non-enzymatic reaction of the free radical coenzyme Q semiquinone. The amount of Q semiquinone is decreased by the metabolism of ketone bodies, thus decreasing the formation of free radicals. The metabolism of ketones also reduces the redox potential of the free cytosolic [NADP+]/[NADPH] ratio thus reducing the potential of the GSH couple facilitating the terminal destruction of oxygen free radicals.

Disclosed herein is the finding that radiation damage to living tissue is lessened by the metabolism of ketone bodies. Based on this surprising discovery, methods of using such ketone esters to reduce or ameliorate or block one or more of the adverse effects of radiation exposure, such as reducing or ameliorating or blocking ionizing radiation tissue damage are disclosed. Thus, the disclosed methods include administering a (R)-3-hydroxybutyrate derivatives and compositions that include these derivatives which serve as precursors to ketone bodies, such as acetoacetate and (R)-3-hydroxybutyrate, and yield elevated circulating concentrations of ketone bodies when administered to a subject; such compositions/derivatives are not plagued with undesirable side effects.

Examples of (R)-3-hydroxybutyrate derivatives include esters of (R)-3-hydroxybutyrate and oligomers of (R)-3-hydroxybutyrate. Disclosed ester compounds include esters derived from alcohols, such as altrose, arabinose, dextrose, erythrose, fructose, galactose, glucose, glycerol, gulose, idose, lactose, lyxose, mannose, ribitol, ribose, ribulose, sucrose, talose, threose, xylitol, xylose, galactosamine, glucosamine, mannosamine, N-acetylglucosamine, mannitol, sorbitol, threitol, (S)-1,2-propanediol and (R)-1,3-butanediol. Advantageously, the method and use of compositions of the present invention is accompanied by fewer or lesser undesirable side effects as it utilizes enhancement of natural energetic pathways to achieve its benefits.

II. Terms

The following explanations of terms and methods are provided to better describe the present disclosure and to guide those of ordinary skill in the art in the practice of the present disclosure.

Alkoxy group: A group represented by the formula —OR, where R can be an alkyl group, including a lower alkyl group, optionally substituted with an alkenyl, alkynyl, aryl, aralkyl, cycloalkyl, halogenated alkyl, or heterocycloalkyl group, as defined below.

Alkyl group: A branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 10 carbon atoms.

Alkenyl group: A hydrocarbon group of 2 to 24 carbon atoms and structural formula containing at least one carbon-carbon double bond.

Alkynyl group: A hydrocarbon group of 2 to 24 carbon atoms and a structural formula containing at least one carbon-carbon triple bond.

Aliphatic group: A group including alkyl, alkenyl, alkynyl, halogenated alkyl and cycloalkyl groups as defined above. A "lower aliphatic group" is an aliphatic group that contains from 1 to 10 carbon atoms.

Aryl group: Any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorous. The aryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl group can be unsubstituted.

Aralkyl: An aryl group having an alkyl group, as defined above, attached to the aryl group. An example of an aralkyl group is a benzyl group.

Administration: Administration of an active compound or composition can be by any route known to one of skill in the art. Administration can be local or systemic. Examples of local administration include, but are not limited to, topical administration, subcutaneous administration, intramuscular administration, intrathecal administration, intrapericardial administration, intra-ocular administration, topical ophthalmic administration, or administration to the nasal mucosa or lungs by inhalational administration. In addition, local administration includes routes of administration typically used for systemic administration, for example by directing intravascular administration to the arterial supply for a particular organ. Thus, in particular embodiments, local administration includes intra-arterial administration and intravenous administration when such administration is targeted to the vasculature supplying a particular organ. Local administration also includes the incorporation of active compounds and agents into implantable devices or constructs, such as vascular stents or other reservoirs, which release the active agents and compounds over extended time intervals for sustained treatment effects.

Systemic administration includes any route of administration designed to distribute an active compound or composition widely throughout the body via the circulatory system. Thus, systemic administration includes, but is not limited to intra-arterial and intravenous administration. Systemic administration also includes, but is not limited to, topical administration, subcutaneous administration, intramuscular administration, or administration by inhalation, when such administration is directed at absorption and distribution throughout the body by the circulatory system.

Analog, derivative or mimetic: An analog is a molecule that differs in chemical structure from a parent compound, for example a homolog (differing by an increment in the chemical structure, such as a difference in the length of an alkyl chain), a molecular fragment, a structure that differs by one or more functional groups, a change in ionization. Structural analogs are often found using quantitative structure activity relationships (QSAR), with techniques such as those disclosed in Remington (*The Science and Practice of Pharmacology*, 19th Edition (1995), chapter 28). A derivative is a biologically active molecule derived from the base structure. A mimetic is a molecule that mimics the activity of another molecule, such as a biologically active molecule. Biologically active molecules can include chemical structures that mimic the biological activities of a compound. It is acknowledged that these terms may overlap in some circumstances.

Animal: Living multi-cellular vertebrate organisms, a category that includes, for example, mammals and birds. The term mammal includes both human and non-human mammals. Similarly, the term subject includes both human and veterinary subjects, for example, humans, non-human primates, dogs, cats, horses, and cows.

Cycloalkyl group: A non-aromatic carbon-based ring composed of at least three carbon atoms. Examples of cycloalkyl groups include, but are not limited to, cyclopropyl, cyclobutyl, cyclopentyl, cyclohexyl, etc.

Derivative: A compound or portion of a compound that is derived from or is theoretically derivable from a parent compound.

Effective amount of a compound: A quantity of compound sufficient to achieve a desired effect in a subject being treated. An effective amount of a compound can be administered in a single dose, or in several doses, for example daily, during a course of treatment. However, the effective amount of the compound will be dependent on the compound applied, the subject being treated, the severity and type of the affliction, and the manner of administration of the compound.

Ester: A term represented by the formula —OC(O)R, where R can be an alkyl, alkenyl, alkynyl, aryl, aralkyl, cycloalkyl, halogenated alkyl, or heterocycloalkyl group, as defined below.

Esterification: A reaction of an alcohol with a carboxylic acid or a carboxylic acid derivative to give an ester.

Halogenated alkyl group: An alkyl group as defined above with one or more hydrogen atoms present on these groups substituted with a halogen (F, Cl, Br, I).

Heterocycloalkyl group: A cycloalkyl group as defined above where at least one of the carbon atoms of the ring is substituted with a heteroatom such as, but not limited to, nitrogen, oxygen, sulfur, or phosphorous.

Hydroxyl group: Represented by the formula —OH.

Mammal: This term includes both human and non-human mammals. Similarly, the term subject includes both human and veterinary subjects, for example, humans, non-human primates, mice, rats, dogs, cats, horses, and cows.

Parenteral: Administered outside of the intestine, for example, not via the alimentary tract. Generally, parenteral formulations are those that will be administered through any possible mode except ingestion. This term especially refers to injections, whether administered intravenously, intrathecally, intramuscularly, intraperitoneally, or subcutaneously, and various surface applications including intranasal, intradermal, and topical application, for instance.

Pharmaceutically acceptable carriers: The pharmaceutically acceptable carriers useful in this disclosure are conventional. *Remington's Pharmaceutical Sciences*, by E. W. Martin, Mack Publishing Co., Easton, Pa., 19th Edition (1995), describes compositions and formulations suitable for pharmaceutical delivery of the compounds herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional nontoxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical agent: A chemical compound or composition capable of inducing a desired therapeutic or prophylactic effect when properly administered to a subject or a cell. Incubating includes exposing a target to an agent for a sufficient period of time for the agent to interact with a cell. Contacting includes incubating an agent in solid or in liquid form with a cell.

Preventing or treating: Preventing refers to inhibiting the full development of something (such as a disease, condition, etc.), for example inhibiting the development of tissue damage after radiation therapy or other exposure to energetic radiation. Treatment refers to a therapeutic intervention that ameliorates a sign or symptom after it has begun to develop.

Radioprotectant/Radioprotection: A cytoprotective substance or composition that prevents or lessens effect(s) of radiation, particularly on cells, biological tissues, organs, or organisms. An optimal radioprotector reduces the latter without significantly compromising the former, and is itself only minimally toxic. Radioprotective agents can be classified as protectants or mitigants: Protectors are administered before exposure to radiation (e.g., radiotherapy (RT) or accidental or unintentional exposure) and are designed to prevent radiation-induced injury. Amifostine is the prototype protectant see, e.g., Kouvaris et al., 12:738-747, 2007. Mitigants are administered after exposure to radiation, but before the phenotypic expression of injury and are intended to ameliorate injury. Palifermin (Kepivance®, Keratinocyte growth factor, KGF; see, e.g., Speilberger et al., *J. Support Oncol.* 2:73-74, 2004) can be considered as the prototype mitigant. Treatment is a strategy that is predominantly palliative and supportive in nature.

Radioprotection allows cells and tissues to survive, and optimally heal and grow, in spite of injury from radiation. Radiation inherently damages tissues. The degree of secondary tissue death and necrosis determines the amount of morbidity and mortality. Radioprotectants attempt reduce, minimize or block the ability of radiation injury to drive cell death. Cell death and tissue damage can be measured by many art known methods. Methods used in vitro and in vivo include biochemical assessment of cell death using functional apoptosis and necrosis assays (e.g., DNA fragmentation, caspase activation, PARP cleavage, annexin V exposure, cytochrome C release, and so forth), morphological changes in cells and tissues, and nuclear fragmentation and loss. In vivo, tissue damage can be assessed by loss of perfusion, scarring, desquamation, alopecia, organ perforation and adhesions, etc.

Radiation: Radiation, as the term is used in physics, is energy in the form of waves or moving subatomic particles emitted by an atom or other body as it changes from a higher energy state to a lower energy state. Common sources of radiation include radon gas, cosmic rays from outer space, and medical x-rays. Radiation can be classified as ionizing or non-ionizing radiation, depending on its effect on atomic matter. The most common use of the word "radiation" refers to ionizing radiation. Ionizing radiation has sufficient energy to ionize atoms or molecules, while non-ionizing radiation does not. Radioactive material is a physical material that emits ionizing radiation. There are three common types of radiation, alpha, beta and gamma radiation. They are all emitted from the nucleus of an unstable atom. X-rays produced by diagnostic and metallurgical imaging and security screening equipment are also ionizing radiation, as are neutrons produced by nuclear power generation and nuclear weapons.

Sources of radiation exposure include, but are not limited to, radiotherapy, nuclear warfare, nuclear reactor accidents, and improper handling of research or medical radioactive materials.

Radiation Dosage: The rad is a unit of absorbed radiation dose defined in terms of the energy actually deposited in the tissue. One rad is an absorbed dose of 0.01 joules of energy per kilogram of tissue. The more recent SI unit is the gray (Gy), which is defined as 1 joule of deposited energy per kilogram of tissue. Thus, one gray is equal to 100 rad.

To accurately assess the risk of radiation, the absorbed dose energy in rad is multiplied by the relative biological effectiveness (RBE) of the radiation to get the biological dose equivalent in rems. Rem stands for "Röntgen Equivalent Man". In SI units, the absorbed dose energy in grays is multiplied by the same RBE to get a biological dose equivalent in sieverts (Sv). The sievert is equal to 100 rem.

The RBE is a "quality factor," often denoted by the letter Q, which assesses the damage to tissue caused by a particular type and energy of radiation. For alpha particles, Q may be as high as 20, so that one rad of alpha radiation is equivalent to 20 rem. The Q of neutron radiation depends on its energy. However, for beta particles, x-rays, and gamma rays, Q is taken as one, so that the rad and rem are equivalent for those radiation sources, as are the gray and sievert.

Radiation Poisoning: Also called radiation sickness or acute radiation syndrome, radiation poisoning involves damage to biological tissue due to excessive exposure to ionizing radiation. The term is generally used to refer to acute problems caused by a large dosage of radiation in a short period, though this also has occurred with long term exposure to low level radiation. Many of the symptoms of radiation poisoning result from ionizing radiation interference with cell division. Beneficially, this same interference enables treatment of cancer cells; such cells are among the fastest-dividing in the body, and in certain instances can be destroyed by a radiation dose that adjacent normal cells are likely to survive.

Symptoms of radiation poisoning include: reduction of red and/or white blood cell count, decreased immune function (with increased susceptibility to infection), nausea and vomiting, fatigue, sterility, hair loss, tissue burns and necrosis, gastrointestinal damage accompanied by internal bleeding, and so forth.

Radiation Therapy (Radiotherapy): The treatment of disease (e.g., cancer or another hyperproliferative disease or condition) by exposure of a subject or their tissue to a radioactive substance. Radiation therapy is the medical use of ionizing radiation as part of cancer treatment to control malignant cells. Radiotherapy may be used for curative or adjuvant cancer treatment. It is used as palliative treatment where cure is not possible and the aim is for local disease control or symptomatic relief.

Subject: Living multi-cellular organisms, including vertebrate organisms, a category that includes both human and non-human mammals.

Therapeutic: A generic term that includes both diagnosis and treatment.

Therapeutically effective amount: A quantity of compound sufficient to achieve a desired effect in a subject being treated.

An effective amount of a compound may be administered in a single dose, or in several doses, for example daily, during a course of treatment. However, the effective amount will be dependent on the compound applied, the subject being treated, the severity and type of the affliction, and the manner of administration of the compound. For example, a therapeutically effective amount of an active ingredient can be measured as the concentration (moles per liter or molar-M) of the active ingredient (such as a small molecule, peptide, protein, or antibody) in blood (in vivo) or a buffer (in vitro) that produces an effect. Exact dosage amounts will vary by the size and other characteristics of the subject being treated, the duration of the treatment, the mode of administration, and so forth.

Transesterification: A reaction of an ester with an alcohol to form a new ester compound.

Treating a disease or disorder: A phrase that is used to describe a therapeutic intervention that ameliorates a sign or symptom of a disease or pathological condition or prevents the disease from appearing, progressing or developing fully.

Under conditions sufficient for/to: A phrase that is used to describe any environment that permits the desired activity.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

Provided herein is a method of protecting human or animal tissue from damage caused by radiation exposure, which method comprises contacting the tissue with an effective amount, such as a therapeutically effective amount, of an agent including a ketone ester, thereby protecting the tissue from radiation damage. In certain embodiments, this method is employed as a method of protecting personnel exposed to a radioactive substance or ionizing radiation, and the method comprises contacting tissue of the personnel with the effective amount, such as therapeutically effective amount, of the agent.

It is contemplated in various examples that contacting is performed within at least one day of before, or during or for up to several days or weeks after exposure to radiation. For instance, in some cases the agent is administered prior to exposure to radiation, during radiation exposure, and/or within two weeks following radiation exposure. In other cases, the agent is administered within days, such as 1 day, 2 days, 3 days, 4 days, 5 days, preferably 6 days or more, including 1 to 3 days, 2 to 4 days, prior to radiation exposure, during radiation exposure, and/or within about 1 day, 2 days, 3 days, 4 days, 5 days or more, including 1 to 3 days, 2 to 4 days following radiation exposure.

In examples of the described methods, the radiation comprises an acute or chronic dose of ionizing or non-ionizing radiation. For instance, the ionizing radiation in some instances results from nuclear fission or fusion or from radioisotopes. In other instances, the ionizing radiation comprises X-rays. In other instances the ionizing radiation comprises radionuclides.

It is also contemplated that the methods described herein are useful where the radiation exposure comprises diagnostic X-rays, radiation therapy, a CAT-scan, a mammogram, a radionuclide scan, or an interventional radiological procedure under CT or fluoroscopy guidance. In other embodiments, the radiation exposure comprises tissue-incorporated radionuclides from ingestion of contaminated food or water, non-medical or unintentional exposure to ionizing radiation from a nuclear weapon, non-medical or unintentional exposure to a radioactive spill, and/or cosmic radiation, including space flight-associated radiation exposure.

In various embodiments, the agent is administered orally, subcutaneously, intramuscularly, intravenously, intraperitoneally, transdermally, intranasally, or rectally.

Also provided herein is use of an agent to reduce, prevent, or treat cell damage from radiation, where the agent is at least one ester of (R)-3-hydroxybutyrate. Disclosed (R)-3-hydroxybutyrate ester compounds include esters described above for other aspects of the disclosure.

IV. Radioprotectant Compounds and Compositions

This disclosure describes radioprotectant compounds and compositions capable of minimizing, reducing and/or preventing tissue damage following intentional and accidental radiation exposure, as well as increasing the therapeutic efficacy of radiation therapies by protecting non-target tissue from incidental radiation damage. These agents also find application in increasing tumor ablation in a patient undergoing radiotherapy. Also provided are pharmaceutical compositions for the treatment of a subject suffering from, or believed to be suffering from, radiation injury, the pharmaceutical composition comprising: a pharmacologically effective amount of radioprotective agent, or a functional analogue thereof, or pharmaceutical composition as identified herein, together with a pharmaceutically acceptable diluent. The disclosure further provides method of treating or preventing radiation injury in a subject in need thereof or in potential need thereof, the method comprising: administering to the subject a pharmaceutical composition comprising: at least one radioprotectant agent that elevates ketone body concentrations, and a pharmaceutically acceptable excipient, in particular wherein the radiation injury comprises irradiation injury.

Particularly provided are compositions for the treatment of a subject that is suspected of having risk of exposure to non-therapeutic radiation. This risk may have been prior to treatment, at the time of treatment or within a few hours post treatment as set out for the method of treatment above.

Exemplary radioprotectants can include those disclosed in U.S. Patent Publication No. 2012/015392, such as acetoacetate, (R)-3-hydroxybutyrate, salts, esters and oligomers of these and conjugates of these with other physiologically acceptable moieties, such as carnitine and other amino acids. Other acceptable materials are metabolic precursors of ketones such as (R)-1,3-butandiol, triacetin, free fatty acids and triglycerides. U.S. Pat. Nos. 4,579,955, 4,771,074, 4,997,976, 5,126,373, 5,420,335, 6,207,856 and 6,306,828, International Application Nos. WO 00/15216, WO 00/04895, and WO 00/14985, Japan Patent Nos. JP 5009185, JP 2885261 and Gueldry et al. (1994) Metabolic Brain Disease Vol 9, No 2, all incorporated herein by reference, are taught as disclosing suitable ketogenic materials.

In some examples, exemplary radioprotectants include those ketone esters, such as esters of (R)-3-hydroxybutyrate derivatives are those described above.

Particular radioprotectant compounds and compositions disclosed herein include ester derivatives of monomeric (R)-3-hydroxybutyrate and ester derivatives or unesterified oligomers including plural (R)-3-hydroxybutyrate residues according to Formulas 1 and 2. With reference to Formulas 1 and 2, n can be any integer, and typically is an integer from 1 to about 100. More typically n is an integer from 1 to about 10. One advantage of the compositions disclosed herein is that they include compounds having defined structures. For example, compositions containing compounds according to Formulas 1 and 2 can be prepared such that the compounds in a given composition have the same number of (R)-3-hydroxybutyrate derivatives (n); such compounds are termed "defined" compounds.

With reference to Formulas 1 and 2, R can be any physiologically compatible alkoxy group. The term "physiologically compatible" refers to alcohols that are substantially non-toxic when released in vivo via esterase or ester cleavage reactions. Certain alcohols are physiologically compatible at low concentration, but can provoke undesired reactions if present at high concentration. For example, ethanol is physiologically compatible at low concentrations but not at high concentrations. Thus ethyl ester (R)-3-hydroxybutyrate derivatives are useful at the lower dosages disclosed herein, but may have undesired effects at the higher dosages.

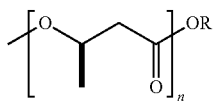

Formula 1

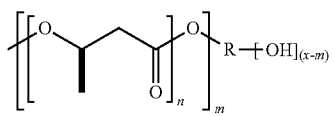

Formula 2

Formula 2, above, represents (R)-3-hydroxybutyrate and its oligomers esterified with monohydric or polyhydric alcohols to yield novel (R)-3-hydroxybutyrate derivatives. Polyhydric alcohols can be acylated at one or more hydroxyl groups. For example, with reference to Formula 2, x represents the number of hydroxyl groups present on the polyhydric alcohol, m represents the number of (R)-3-hydroxybutyrate oligomers attached to R via ester bonds and n represents the number of (R)-3-hydroxybutyrate residues per oligomer. For example if R is an alcohol that has 5 hydroxyl groups and three are esterified with (R)-3-hydroxybutyrate (making n equal to 1), x is 5, m is 3 and x-m equals 2.

With reference to Formula 2, R can contain any number (x) of hydroxyl groups. In several embodiments R is a monosaccharide having 4 or 5 hydroxyl groups. Thus in these embodiments R can have from 1 to 5 (R)-3-hydroxybutyrate groups or (R)-3-hydroxybutyrate oligomers appended via an ester bond. In other embodiments R contains more than 5 hydroxyls, for example when R is an oligosaccharide derivative. In exemplary embodiments R is a diol (x equal to 2), such as 1,2-propanediol or a triol (x equal to 3), such as 1,3-butanediol, glycerol or threitol. Exemplary disclosed compounds according to Formula 2 are described in Table 1, below.

TABLE 1

| Alcohol/number of hydroxyls (x) | (R)-3-hydroxybutyrate residues (n) | ester bonds (m) |
|---|---|---|
| (R)1,3-butanediol/2 | 3 | 1 |
| (R)1,3-butanediol/2 | 3 | 2 |
| glycerol/3 | 3 | 3 |
| glucose/5 | 1 | 5 |
| galactose/5 | 5 | 1 |
| galactose/5 | 3 | 4 |
| mannitol/6 | 2 | 6 |

TABLE 1-continued

| Alcohol/number of hydroxyls (x) | (R)-3-hydroxybutyrate residues (n) | ester bonds (m) |
|---|---|---|
| sucrose/7 | 1 | 7 |
| sucrose/7 | 3 | 7 |
| sucrose/7 | 6 | 1 |

In Formula 2, the (R)-3-hydroxybutyrate oligomers include the same number of (R)-3-hydroxybutyrate residues, however this is not necessary. For example, a (R)-3-hydroxybutyrate derivative can include two or more different oligomers having different lengths.

In certain embodiments, a polyhydric alcohol for incorporation into (R)-3-hydroxybutyrate derivatives is (R)-1,3-butanediol. This diol can be selectively acylated with (R)-3-hydroxybutyrate and oligomers thereof at one or both hydroxyl groups. Thus, exemplary embodiments include compounds according to Formulas 3 and 4, shown below. With respect to Formula 3, n and m can be the same or different.

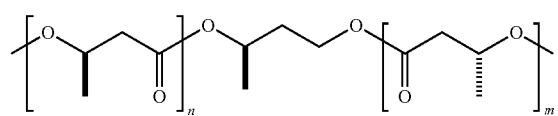

Formula 3

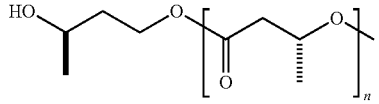

Formula 4

Because (R)-3-hydroxybutyrate derivatives according to Formulas 3 and 4 release (R)-1,3-butanediol in vivo, which is oxidized to (R)-3-hydroxybutyrate and acetoacetate in the liver, (R)-1,3-butanediol is a particularly useful physiologically compatible alcohol for preparing (R)-3-hydroxybutyrate derivatives.

In one embodiment, the compositions include mixtures of (R)-3-hydroxybutyrate derivatives. For example, two or more (R)-3-hydroxybutyrate ester derivatives according to Formulas 1, 2 or both can be formulated and administered in the same composition Compositions disclosed herein typically are nontoxic, sterile and pyrogen free, particularly endotoxin free. The compositions can be formulated in a palatable form for administration as a food additive or supplement. Such palatable forms are typically odor free or are masked or coated as is known to those of ordinary skill in the art of pharmaceutical formulation. Suitable formulations are described in WO 11/101171 which is hereby incorporated by reference in its entirety. Pharmaceutical formulations can include additional components, such as carriers. The pharmaceutically acceptable carriers useful for these formulations are conventional. *Remington's Pharmaceutical Sciences*, by E. W. Martin, Mack Publishing Co., Easton, Pa., 19th Edition (1995), describes compositions and formulations suitable for pharmaceutical delivery of the compounds herein disclosed.

Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (for example, sorbitol syrup, cellulose derivatives or hydrogenated edible fats); emulsifying agents (for example, lecithin or acacia); non-aqueous vehicles (for example, almond oil, oily esters, ethyl alcohol or fractionated vegetable oils); and preservatives (for example, methyl or propyl-p-hydroxybenzoates or sorbic acid). The preparations can also contain buffer salts, flavoring, coloring, and sweetening agents as appropriate which are known to those of ordinary skill in the art. The compounds also can be added to liquid vitamin formulations and electrolyte containing drinks. Drinks may be in the form of energy drinks, sports drinks, fruit drinks, citrus drinks, carbonated drinks, dry drink mixes, other suitable drink mediums or combinations thereof.

In some embodiments where the disclosed compounds are administered orally, particularly when they are administered as a nutritional supplement, the compounds can be mixed with a foodstuff base. Such mixtures can be in the form of an emulsion or an admixture with solid food. For example, health bars, without limitation, can be prepared by combining various excipients, such as binders, fillers, flavorings, colorants and the like, along with one or more (R)-3-hydroxybutyrate derivatives, and mixing to a plastic mass consistency. The mass is then either extruded or molded to form "candy bar" shapes that are then dried or allowed to solidify to form the final product.

For topical administration, the compounds can be, for example, mixed with a liquid delivery agent for administration locally. The agents used therapeutically are readily soluble or suspendable in water and saline, and as such these would be useful for delivery since water or saline do not cause adverse biological tissue effects. This allows sufficiently high doses to be administered locally or systemically, without secondary toxicity from the delivery vehicle.

Generally, the formulations are prepared by combining the therapeutic agent(s) each uniformly and intimately with liquid carriers or finely divided solid carriers or both. Then, if necessary, the product is transformed into the desired formulation. Optionally, the carrier is a parenteral carrier, and in some embodiments it is a solution that is isotonic with the blood of the recipient. Examples of such carrier vehicles include water, saline, Ringer's solution, and dextrose solution. Non-aqueous vehicles such as fixed oils, medium chain triglycerides (MCTs) and ethyl oleate are also useful herein.

To maintain elevated blood ketone body concentrations over a 24 hour period, delayed release formulations can be used. The release of the (R)-3-hydroxybutyrate derivatives can be controlled by a number of formulation techniques. For example, techniques such as enteric coatings, film coatings, microencapsulation and the like can be used to retard release of the (R)-3-hydroxybutyrate derivatives as is known to those of ordinary skill in the art. In the case of the preferred ketone ester of Formula I this itself provides a sustained generation of ketosis over a period of hours.

Also contemplated is application of the provided radioprotectant agents via an autoinjector. Thus, another embodiment is the pharmaceutical composition comprising a described radioprotectant agent which is contained in an autoinjector. An autoinjector is a medical device designed to deliver a single dose of a particular (typically life-saving) drug, sometimes also described as a pre-filled syringe for self-injection or for injection by non-medical personnel.

Autoinjectors are, for example, as described in U.S. Pat. Nos. 6,149,626, 6,099,504, 5,957,897, 5,695,472, 5,665,071, 5,567,160, 5,527,287, 5,354,286, 5,300,030, 5,102,393, 5,092,843, 4,894,054, 4,678,461, and 3,797,489, the contents of each such patent being incorporated herein by reference.

The disclosure therefore provides such an autoinjector useful for the treatment of (ir)radiation injury irrespective of whether the radiation is emitted by radioactive substances (radioisotopes), such as uranium, radon, and plutonium, or is produced by man-made sources, such as x-ray and radiation therapy machines. Also provided are autoinjectors comprising a pharmaceutical composition consisting of a radioprotective agent and a suitable excipient.

The therapeutic agents can also be administered directly as part of a surgical or other medical procedure, or at the bedside by a treating physician. Drug quality product can be diluted for instance in sterile saline and given by injection using sterile 1 cc syringes and small bore needles (25 gauge and less) to a subject in need of radioprotection. Alternatively, a wound bed can be irrigated for instance with a saline or other therapeutically effective solution containing a known concentration (dosage) of drug or compound, or a combination thereof. Precise control and localization of therapeutic effects can thus be obtained.

Controlled release parenteral formulations can be made as implants, oily injections, or as particulate systems. For a broad overview of protein delivery systems, see Banga, *Therapeutic Peptides and Proteins: Formulation, Processing, and Delivery Systems*, Techonomic Publishing Company, Inc., Lancaster, Pa., 1995. Particulate systems include microspheres, microparticles, microcapsules, nanocapsules, nanospheres, and nanoparticles.

Alternatively, the compound may be administered in a gel, lotion, ointment or other suitable form which is applied to the tissue up to about 90 minutes before irradiation or treatment and remains on the tissue during and optionally after the treatment.

The same dosage and concentrations can be used when the radioprotective agent is administered after irradiation and/or radiotherapeutic treatment. The three administrations (before, during and after radiotherapy treatment) may be used alone, or in any combination of two or all three administrations, as needed.

The disclosed radioprotective agents including at least one ketone ester are stable at room temperature and can be stored for use in case of a radiological event such as a terrorist nuclear bomb or nuclear power plant malfunction. For example, subjects exposed to radiation at between and including 50 to 400 rad can be treated with a disclosed radioprotective agent including one or more ketone esters at 150 grams/subject/day for 1 to 5 days or more than 5 days if required. If subjects are not capable of receiving oral administration (too severely burned or injured), subject can be administered a disclosed radioprotective agent, such as the sodium salt of D-β-hydroxybutyrate, intravenously.

V. Methods for Preparing (R)-3-Hydroxybutyrate Derivatives

The disclosed (R)-3-hydroxybutyrate derivatives used as radioprotectants herein can be produced using chemical techniques, enzymatic techniques, transgenic organisms, or combinations thereof, including those disclosed in U.S. Patent Publication No. US-2006-0280721-A1, which is hereby incorporated by reference in its entirety. In one embodiment, polymers of (R)-3-hydroxybutyrate (poly-(R)-3-hydroxybutyric acid), such as naturally occurring polymers, which are commercially available from, for example, Aldrich, Milwaukee, Wis., are converted to the thermodynamically favored cyclic trimer (triolide) by the method of Seebach and coworkers. See, Seebach et al., *Eur. J. Biochem.* 1994, 224, 317-328; *Helv. Chim. Acta* 1982, 65, 495-503; and *Angew. Chem. Int. Ed. Engl.* 1992, 31, 434, 435, all of which are incorporated herein by reference.

The triolide is a versatile intermediate that can be converted to several different (R)-3-hydroxybutyrate derivatives. Exemplary ester derivatives, such as those according to Formula 1 and 2, can be produced from the triolide by chemical and/or chemoenzymatic methods. In one example of a chemoenzymatic method, the triolide is treated with a lipase in the presence of (R)-1,3-butanediol to afford the novel ester product shown in Scheme 1, below.

Scheme 1

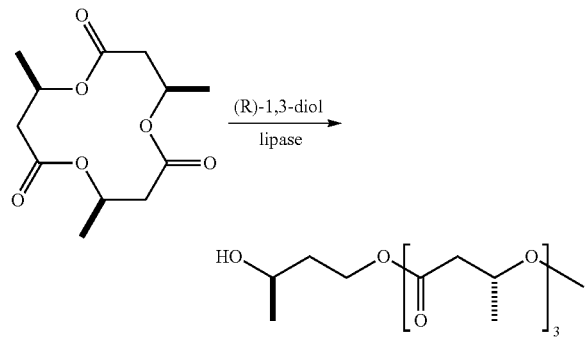

Additional methods for making (R)-3-hydroxybutyrate derivatives include esterifying or transesterifying linear oligomers of (R)-3-hydroxybutyrate and transesterifying cyclic (R)-3-hydroxybutyrate oligomers containing four or more (R)-3-hydroxybutyrate residues. For example, (R)-3-hydroxybutyrate oligomers having defined length can be produced by enzymatic depolymerization of poly-(R)-3-hydroxybutyric acid. Specifically, Wang et al. (*Biomacromolecules* 2002, 3, 838-834, this publication is incorporated herein by reference) have reported conditions for producing the (R)-3-hydroxybutyrate dimer via depolymerization. The (R)-3-hydroxybutyrate dimer can be esterified with an alcohol to yield, for example, compounds according to Formula 5.

Formula 5

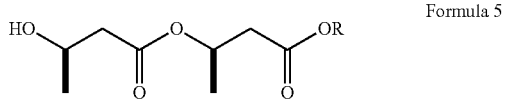

In one embodiment, polymers of (R)-3-hydroxybutyrate (poly-(R)-3-hydroxybutyric acid), are converted to (R)-3-hydroxybutyrate and/or oligomers thereof via acid catalyzed depolymerization. In one aspect, the depolymerization is performed in supercritical carbon dioxide that includes water as a cosolvent. The pH of water in contact with supercritical carbon dioxide is approximately 2.9 due to the formation of carbonic acid, which can accelerate the depolymerization reaction (Toews, et al. *Anal. Chem.* 1995, 67, 4040). Optionally, an acid catalyst can be added to the supercritical carbon dioxide to promote the depolymerization reaction. Suitable acid catalysts are known to those of ordinary skill in the art and include, for example, organic acids, such as 4-toluenesulfonic acid.

In another example of acid catalyzed depolymerization, a Lewis acid is used to promote the depolymerization reaction. For example, Seebach et al. Helv. Chim. Acta 1982, 65, 495-503, disclose a titanium catalyzed transesterification protocol for producing ethyl (R)-3-hydroxybutyrate from poly-(R)-3-hydroxybutyric acid.

In another embodiment, (R)-3-hydroxybutyrate is prepared from ethyl acetoacetate, which is readily available from various commercial sources. For example, as is known to those of ordinary skill in the art, ethyl acetoacetate can be reduced stereospecifically using chemical or enzymatic techniques to give the desired (R)-3-hydroxybutyrate product. Similarly, ethyl acetoacetate can be reduced at the carboxylate carbon either before or after the stereospecific reduction to afford (R)-1,3-butanediol. Beta keto esters, such as ethyl acetoacetate, can be stereospecifically reduced both enzymatically, using for example a dehydrogenase, and chemically using various catalysts as is well known to those of ordinary skill in the art. For example, Brown et al. *J. Org. Chem.* 1989, 54, 1577-1583; and *J. Org. Chem.* 1989, 54, 4504-4511, describe the stereospecific reduction of such beta keto ester compounds using alkyl borane complexes. Additional suitable methods that employ catalytic ruthenium complexes have been reviewed by Everaere et al. *Adv. Synth. Catal.* 2003, 345, 67-77. The Brown and Everaere publications are incorporated herein by reference. A catalytic system for enzymatically preparing (R)-3-hydroxybutyrate from ethyl acetoacetate is described in the examples section below.

In one embodiment, polymers of (R)-3-hydroxybutyrate are converted to useful (R)-3-hydroxybutyrate oligomers and derivatives thereof by using enzymatic catalysis. These enzymatic methods also can be used to produce intermediates of useful (R)-3-hydroxybutyrate-containing compounds. For example, numerous polyhydroxyalkanoate depolymerase enzymes are produced in various bacteria and can be expressed as is known to those of ordinary skill in the art. For a review, see Jendrossek, D. *Extracellular PHA Depolymerases—the Key Enzyme of PHA Degradation.* In: Biopolymers. Part 3b, Polyesters, (Steinbüchel and Doi Eds.) pp. 41-83. Wiley-VCH, Weinheim, The Jendrossek review is incorporated herein by reference. Useful depolymerase enzymes include the family PhaZ1-PhaZ7, from the subgroup EC 3.1.1.75, which are produced by the polyhydroxyalkanoate-degrading bacterium *Paucimonas lemoignei* can be used to convert poly-(R)-3-hydroxybutyric acid to (R)-3-hydroxybutyrate and oligomers thereof. PhaZ5, for example, can be produced via expression in *Bacillus subtilis*, as described by Braaz et al. *FEMS Microbiol. Lett.* 2002, 209, 237-241, which is incorporated herein by reference. Similarly, PhaZ7 can be produced from *Paucimonas lemoignei* as described by Handrick et al. *J. Biol. Chem.* 2001, 276, 36215-36224 and Braaz et al. *FEMS Microbiol. Lett.* 2003, 224, 107-112, and used to produce useful oligomeric (R)-3-hydroxybutyrate derivatives. Both of these publications are incorporated herein by reference. The depolymerase and conditions for depolymerization can be selected by those of ordinary skill in the art based upon the product or mixture of products desired. For example, in certain embodiments disclosed herein it is desirable to produce oligomers of (R)-3-hydroxybutyrate, such as dimers, trimers, tetramers, pentamers, and the like, while minimizing the presence of (R)-3-hydroxybutyrate monomer. PhaZ7, for example, favors the (R)-3-hydroxybutyrate pentamer. In certain other embodiments (R)-3-hydroxybutyrate monomer is the desired product. Oligomers and ester derivatives thereof containing seven or fewer (R)-3-hydroxybutyrate units have been demonstrated to yield particularly desirable blood ketone body concentrations upon oral administration. However (R)-3-hydroxybutyrate octamers and higher oligomers and derivatives thereof also are useful as therapeutics and nutritional supplements.

Methods for preparing higher oligomers of (R)-3-hydroxybutyrate can employ enzymatic depolymerization techniques, as discussed above, or can use conventional synthetic chemistry techniques. For example, oligomeric (R)-3-hydroxybutyrate can be prepared by iterative esterification of (R)-3-hydroxybutyrate according to the method taught by U.S. Pat. No. 5,625,030 to Williams et al. (Williams), which is incorporated herein by reference. Such oligomeric (R)-3-hydroxybutyrate compounds can be esterified with a physiologically compatible alcohol by the methods disclosed by Williams, and those reviewed in Haslam, E. Tetrahedron 1980, 36, 2409-2434, which is incorporated herein by reference. Thus, (R)-3-hydroxybutyrate oligomers having any length can be prepared and used to produce the therapeutic (R)-3-hydroxybutyrate derivatives disclosed herein.

In one example a (R)-3-hydroxybutyrate oligomer is prepared as shown in Scheme 2, below. With reference to Scheme 2, the (R)-3-t-butyldimethylsilyloxybutyrate derivative can be prepared under the conditions disclosed by Greene and Wuts in *Protective Groups in Organic Synthesis*, 3rd ed.; Wiley-Interscience, New York, (1999), which is incorporated herein by reference. Step one in Scheme 2 is attaching the protected (R)-3-hydroxybutyrate derivative to a solid support as taught by Barlos and coworkers (Barlos et al. Tetrahedron Lett. 1989, 30, 3947; ibid. 3943, both of which are incorporated herein by reference). Step 2 is selective deprotection of the solid support-bound (R)-3-hydroxybutyrate derivative. Suitable conditions for this reaction include using fluoride sources as taught by Greene and Wuts, an exemplary reagent for this reaction is TAS-F, which is commercially available from Aldrich, Milwaukee, Wis. (See, Roush et al. *J. Org. Chem.* 1998, 63, 6436, which is incorporated herein by reference). Other suitable reagents for accomplishing step 2 in Scheme 2, including other fluoride sources, are well-known to those of ordinary skill in the art of synthetic chemistry. With reference to step 3, a second (R)-3-hydroxybutyrate derivative is introduced by a condensation reaction. Suitable conditions for this condensation include using a carbodiimide reagent, such as diisopropylcarbodiimide (DIC) or dicyclohexylcarbodiimide, optionally in combination with a catalytic amount of dimethylaminopyridine (DMAP). Additional suitable reaction conditions for step 3 are disclosed in the Williams patent. Optionally, steps 2 and 3 can be repeated any number of times to provide (R)-3-hydroxybutyrate oligomers of a desired length. Step 4, cleavage, involves treatment of the solid support-bound (R)-3-hydroxybutyrate derivative with an acid, typically a weak acid, such as acetic acid. Specific conditions involve treating the solid support with an acetic acid, trifluoroethanol, dichloromethane mixture (2:2:6 ratio) for approximately two hours at room temperature.

Scheme 2

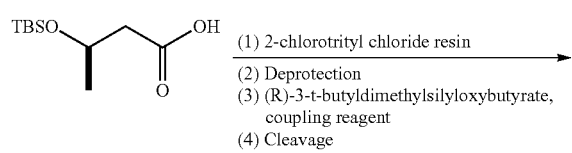

(1) 2-chlorotrityl chloride resin
(2) Deprotection
(3) (R)-3-t-butyldimethylsilyloxybutyrate, coupling reagent
(4) Cleavage -continued

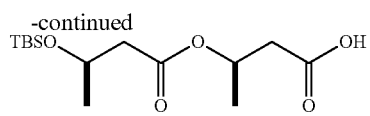

One or more equivalents of the product provided in Scheme 2 can be esterified with a physiologically compatible alcohol. For example, if the alcohol is a polyhydric alcohol, the stoichiometry of the reaction can be chosen so that each hydroxy group of the alcohol is esterified with the dimeric (R)-3-hydroxybutyrate derivative. Esterification of the defined oligomeric (R)-3-hydroxybutyrate derivatives produced as described herein can be esterified as taught by U.S. patent application Ser. No. 09/359,086, to Martin et al., which is incorporated herein by reference. Moreover, numerous suitable esterification conditions are disclosed by the Williams patent, and other conditions are well known to those of ordinary skill in the art. Removal of the silyl group from the resulting ester compound using conditions disclosed by Greene and Wuts, affords the desired (R)-3-hydroxybutyrate derivative.

Another chemical method for preparing oligomers containing two or more (R)-3-hydroxybutyrate residues uses (R)-3-hydroxybutyrate as a starting material. For example, Seebach and coworkers describe using the corresponding acid chloride derivative of 3-hydroxybutyrate to assemble 3-hydroxybutyrate oligomers in solution (Seebach et al. *Helv. Chim. Acta* 1988, 71, 155-167, which is incorporated herein by reference). Acid chlorides also can be formed from 3-hydroxybutyrate oligomers. For example, the acid chloride of the dimeric compound prepared according to Scheme 2, above, can be prepared according to the method of Seebach et al. The corresponding acid chloride can be reacted with physiologically compatible alcohols to afford, after deprotection, exemplary novel (R)-3-hydroxybutyrate derivatives.

The various alcohols for preparing (R)-3-hydroxybutyrate derivatives can be produced by any method that affords the desired physiologically compatible alcohol. An exemplary alcohol, (R)-1,3-butanediol, can be produced from (R)-3-hydroxybutyrate via reduction of the carboxylic acid moiety. Reagents and methods for reducing the carboxylic acid group are found in R. C. Larock, Comprehensive Organic Transformations, VCH publishers, 1989, pp. 432-434, which is incorporated herein by reference. This route is particularly convenient because (R)-3-hydroxybutyrate is readily available as a single enantiomer from several sources. For example, (R)-3-hydroxybutyrate can be produced via enzymatic depolymerization of its naturally occurring polymer. For exemplary methods, see Shang et al. *Appli. Environ. Microbiol.* 1994, 60, 1198-1205, and U.S. Pat. No. 6,472,188 to Lee et al., both of which are incorporated herein by reference. The poly-(R)-3-hydroxybutyric acid starting material for the depolymerization methods can be produced by any of several methods, examples of which are taught in U.S. Pat. No. 5,569,595 to Dennis and U.S. Pat. No. 6,492,134 to Aquin.

In another example, lipase catalyzed esterification of (R)-1,3-butanediol with the triolide compound yields the novel bis-esterified diol according to Scheme 3, below. The reaction pathways of Scheme 1 and Scheme 3 can be selected by using different lipase enzymes and/or varying reaction conditions, such as reagent concentration and stoichiometry as is known to those of ordinary skill in the art.

Scheme 3

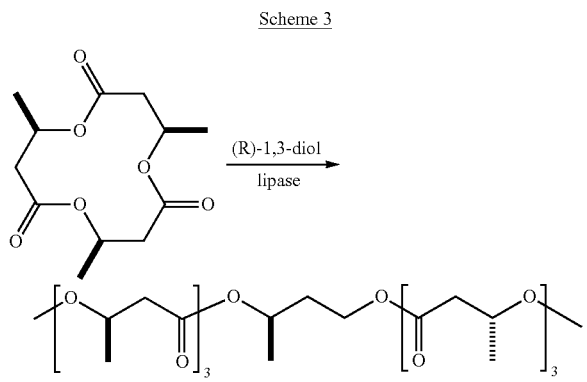

Typically, lipases carry out their customary reactions, the hydrolysis of ester bonds, in aqueous solvents. However in organic solvents, where water is substantially excluded, lipases can efficiently catalyze esterification reactions. These enzymes can be used to esterify a wide variety of substrates and also can catalyze transesterification reactions. Unfortunately, the use of organic solvents has several drawbacks, particularly for pharmaceutical and food industry applications. For example, organic solvents are expensive and often flammable. Moreover, many organic solvents are toxic and therefore organic solvent contamination in pharmaceutical or nutritional products can be a serious problem. Thus it is desirable that pharmaceutical and nutritional products are free from solvent contamination, which introduces additional complications and expense.

Prior attempts to use metabolic precursors of ketone bodies, such as (R)-3-hydroxybutyrate derivatives also have been unsuccessful in part due to the methods used to prepare such derivatives. Current methods for preparing (R)-3-hydroxybutyrate derivatives also limit the use of these compounds due to the high cost of the product and the introduction of product contamination inherent in the methods. For example, preparations of such derivatives that employ organic solvents are costly and can contaminate the product with toxic solvent residue.

One embodiment for making (R)-3-hydroxybutyrate derivatives overcomes the drawbacks of using organic solvents by using supercritical fluids, particularly supercritical carbon dioxide as a reaction medium. Supercritical fluids are by definition at a temperature and pressure greater than or equal to the critical temperature and pressure of the fluid. Carbon dioxide's critical pressure is about 7,370 kilopascals (kPa) and critical temperature is about 31 degrees Celsius (° C.), so supercritical applications using carbon dioxide typically operate at temperatures between about 32° C. and 49° C. and pressures between about 7,370 and 24,000 kPa. Supercritical solvents, particularly supercritical carbon dioxide, provide many advantages over conventional organic solvents. For example, carbon dioxide is an environmentally benign reaction medium. An exemplary method for performing enzymatic reactions in supercritical fluids is disclosed by U.S. Pat. No. 5,783,627 to Kao et al., which is incorporated herein by reference. Unlike conventional organic solvents, carbon dioxide can be allowed to simply evaporate without leaving a contaminating residue. Thus, the use of carbon dioxide simplifies both disposal and purification protocols.

In certain examples, the reaction medium can include supercritical carbon dioxide and a cosolvent. The cosolvent can include water and/or one or more organic cosolvents. Types of organic cosolvents include polar and non-polar cosolvents. Examples of polar organic cosolvents include methanol, ethanol, tetrahydrofuran, acetone and the like. Examples of suitable nonpolar cosolvents include hexanes, cyclohexane, toluene and the like.

Both the enzymatic and non-enzymatic methods for preparing (R)-3-hydroxybutyrate derivatives disclosed herein can be performed in supercritical carbon dioxide. However, supercritical carbon dioxide has a pH of between about 4 and about 5. This acidic pH can denature some proteins, thereby abrogating their catalytic activity. Thus, in one aspect of the method for making (R)-3-hydroxybutyrate derivatives, stabilized lipases, such as crosslinked enzyme crystal (CLEC) lipases are used. Examples of methods for making and using such stabilized lipases are disclosed in U.S. Pat. No. 5,618,710 to Navia et al. and U.S. Pat. No. 6,211,422 to DeSimone et al., both of which are incorporated herein by reference.

In another aspect, pH sensitive lipases can be used within their effective pH range by incorporating a buffer into the solvent system. Examples of buffer systems for particular pH ranges are given by Ellis and Morrison (*Methods Enzymol.* 1982, 87, 405) and by McLellan (*Anal. Biochem.* 1982, 126, 94), both of which are incorporated herein by reference. Additional suitable buffers for a given pH range are known to those of ordinary skill in the art.

Suitable lipases for preparing (R)-3-hydroxybutyrate derivatives can be selected based upon the desired derivative. For example, lipases can be screened for the ability to catalyze a desired reaction by the protocol described in Example 1, below. Suitable lipases for screening to determine the optimal catalyst are disclosed by Whitesides and Wong (1994, *Enzymes in Synthetic Organic Chemistry*, Elsevier, Oxford), Gross et al. (*Chem. Rev.* 2001, 101, 2097-2124) and Michor et al. (*Biotechnology Letters* 1996, 18, 79-84), these references are incorporated herein by reference. A source for suitable lipases is Biocatalytics, Inc., Pasadena, Calif., which sells a screening set of lipases under the trade name "CHIRAZYME." It is currently believed that porcine pancreatic lipase (PPL), the lipase from *P. cepacia* (lipase PC), and *Pseudomonas* sp. lipase (PSL) are particularly useful lipases for preparing (R)-3-hydroxybutyrate esters.

Immobilized lipases are useful for preparing (R)-3-hydroxybutyrate esters. Immobilized lipases provide advantages in efficiency, catalytic turnover and ease of product purification. Lipases can be immobilized on any substrate, with typical examples including glass or gold surfaces, polymer beads, silica, Celite and the like. U.S. Pat. No. 6,080,402 to Reetz et al. and U.S. Pat. No. 6,398,707 to Wu et al., which are incorporated herein by reference, describe useful lipase immobilization techniques.

In other embodiments, the (R)-3-hydroxybutyrate derivatives disclosed herein can be produced, or intermediates to the derivatives can be produced, by microorganisms. For example, in one embodiment poly-(R)-3-hydroxybutyric acid is used as a starting material for producing compounds according to Formulas 1 and 2. The genes responsible for producing poly-(R)-3-hydroxybutyric acid have been cloned and expressed, and this material can be produced in several different microorganisms under a variety of conditions. See, Rhie and Dennis, *Appl. Environ. Microbiol.* 1995, 61, 2487-2492, which is incorporated herein by reference. Poly-(R)-3-hydroxybutyric acid can be converted into the therapeutic compounds disclosed herein by chemical methods, enzymatic methods, and combinations thereof. In another embodiment, the poly-(R)-3-hydroxybutyrate derivatives are produced completely in microorganisms.

VI. Therapeutic Uses

The increased use of radionuclides in diagnostic and therapeutic nuclear medicine, as well as the presence of man-made and naturally occurring radioactivity in the environment, emphasizes the need for radioprotective agents for protection of cells, tissues and organisms before, during, and after exposure to radiation. The radioprotective agents described herein enable survival of living organisms in otherwise lethal radiation exposure conditions, and provide reduction of cellular and tissue damage from exposure to non-lethal levels of radiation.

The newly identified radioprotective agents described herein, administered prior to, during, and/or after exposure to radiation, can eliminate or reduce the severity of deleterious cellular effects caused by exposure to environmental ionizing radiation such as resulting from a nuclear explosion, a spill of radioactive material, close proximity to radioactive material and the like. The agents also provide dramatic protection of normal tissue exposed to therapeutic radiation used for cancer therapy.

The present invention provides methods which protect cells and living organisms from deleterious cellular effects by preventing or eliminating these effects or by reducing their severity. According to the present invention, living organisms to be protected can be exposed with an agent that increases ketone bodies prior to, after, or during exposure of the cell to radiation. The cells may be directly treated by the radioprotective agent, such as by applying a solution of a radioprotective agent of the disclosure to the cell or by administering a radioprotective agent as described to a mammal. The compounds of the present invention thus can provide a protective effect in the cell and living organisms which eliminates or reduces the severity of the detrimental cellular effects which would otherwise be caused by the exposure.

It will be recognized that any and all tissue, skin or hair follicles can be treated or protected topically in accordance with the present invention.

Radioprotectants to Prevent or Treat Radiation Damage

Radioprotective agents of the present disclosure can be used to minimize or prevent the damage from solar radiation exposure experienced by astronauts, pilots, other flight personnel and frequent fliers. The radioprotective agents can also be utilized in protecting from accidental radiation exposure from nuclear power facilities, other radiation generating facilities including those for food irradiation, or as a result of detonation of an atomic bomb or other device that releases radiation or radioisotopes. Also, they can be used to confer protection to those personnel involved with clean-up of such radiation accidents or disposal facilities. The radioprotective agents of the present invention are also of use in reducing the toxic effects of inhaled or ingested radionuclides and in reducing toxicity from radiation produced by electronic devices of non-ionizing nature of radiation: such as cellular telephones, and microwaves.

Rapidly growing interventional radiologic procedures such as dilatation of stenosed vessels, recanalization or vascular angioanastomoses would also benefit from the use of radioprotectors.

Additionally, therapy and diagnostic tests utilizing radiation are withheld from pregnant women, women who may be pregnant, and women capable of becoming pregnant to avoid harming the fetus in utero. This can often preclude necessary treatment or diagnosis for these women. Accordingly, radioprotective agents that are non-toxic and highly effective can be administered to such women so as to confer protection on the women and any possible fetus above and beyond any conventional mechanical radiation shielding device. This can also provide a level of safety to those women nursing their infants.

Radioprotectants to Enhance Radiotherapy

In addition, the radioprotective agents described herein are believed to provide a selective protection of normal cells, and not of cancer cells, during cancer radiation therapy. For example, these agents, administered to a cancer patient prior to or during radiation therapy, will provide protection to normal, non-cancer cells while allowing the radiation treatment to destroy cancerous cells. Therefore, the radioprotective agents would provide a selective protective effect on the normal cells as compared to tumor cells and would eliminate or reduce the severity of deleterious or other detrimental side effects of radiation therapy on normal cells and tissues.

Radioprotective agents thus are useful in eliminating or reducing the severity of deleterious cellular effects in normal cells caused by cancer radiation therapy and diagnostic tests utilizing radiation.

For example, the treatment of malignant tumors through the use of radiation is often limited due to damage to non-tumor cells. Damage to the non-tumor cells can compromise the effectiveness of the radiation therapy. The dominant consideration in establishing radiation doses for cancer radiotherapy is the assessment of tolerance of the most radiosensitive normal tissue or organ in the treatment field. This assessment, together with the expected radiation dose required to eradicate a tumor determines the feasibility of the treatment strategy, and whether a cure or palliation is to be attempted. Often, the maximum tolerable doses are insufficient to eradicate the tumor. Thus, the use of a radioprotective agent such as those provided herein would greatly increase the tolerable dose, and therefore the prospects for eradication of tumors and treatment of the cancer.

More particularly, provided herein are methods of protecting non-cancer, or normal, cells of a mammal from deleterious cellular effects caused by exposure of the mammal to ionizing radiation. The radioprotective agents described herein provide protection of normal cells during intentional exposure to radiation, such as during radiation therapy or diagnostic procedures such as x-rays and CAT scans. The cancer cells, if protected at all are believed to be protected to a lesser extent than normal cells. Despite a moderate protection in vitro, the cancer cells are rendered more sensitive to radiation in vivo, resulting in greater tumor ablation by radiotherapy. Thus, the inventors provide methods whereby the deleterious cellular effects on non-cancer cells caused by exposure of the mammal to radiation are eliminated or reduced in severity or in extent.

VII. Combination Therapies

The immediate damage caused by radiation is mediated by formation of highly reactive free radicals inside the cell such as hydroxyl, peroxide, and carbonate radicals. These rapidly react with sensitive macromolecules such as DNA to cause permanent cell damage and eventual cell death. Chemical radioprotectants limit this immediate damage by directly neutralizing reactive radicals. The radioprotectants embodied in the subject disclosure are not directed to this immediate chemical damage but permit the cell to repair the immediate damage without triggering a suicide response. Therefore, combinations of the present embodiments with chemical protectants, such as thiols, that act by directly scavenging free radicals would be useful. Such combination would be particularly useful in cases where advance warning of radiation exposure is possible, but may have less advantage post-exposure, where chemical radioprotectants are less effective.

The foregoing disclosure is further explained by the following non-limiting example.

EXAMPLE

This example demonstrates how ketone bodies protect tissues from damage caused by ionizing radiation.

The methods used in the studies of cultured cells were the same as previously reported in Miller A. C. et al., *Int. J. of Radiation Biol.* 1997, 72: 211-18. The ester composition used was the mono R 3 hydroxybutyryl-R-1,3 butanediol enantiomerically enriched in the 1 position of R-1,3 butanediol.

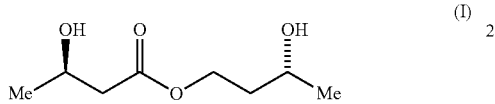
(I)

Figure 2:
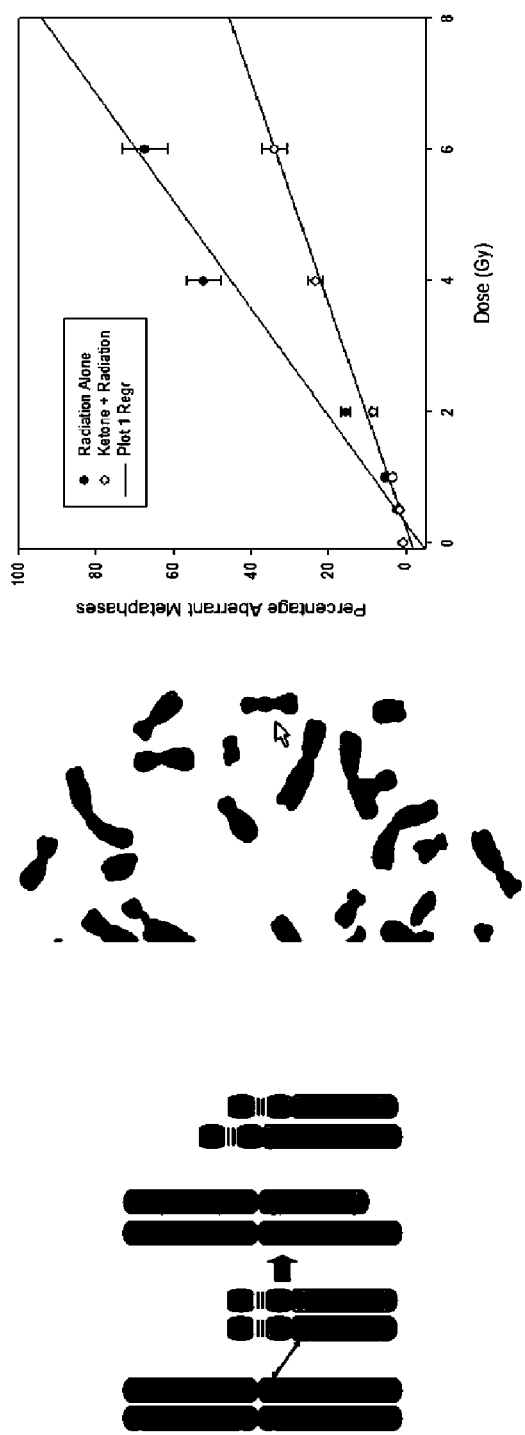
FIG. 2 illustrates chromosomal protection by ketone esters.
Figure 3:
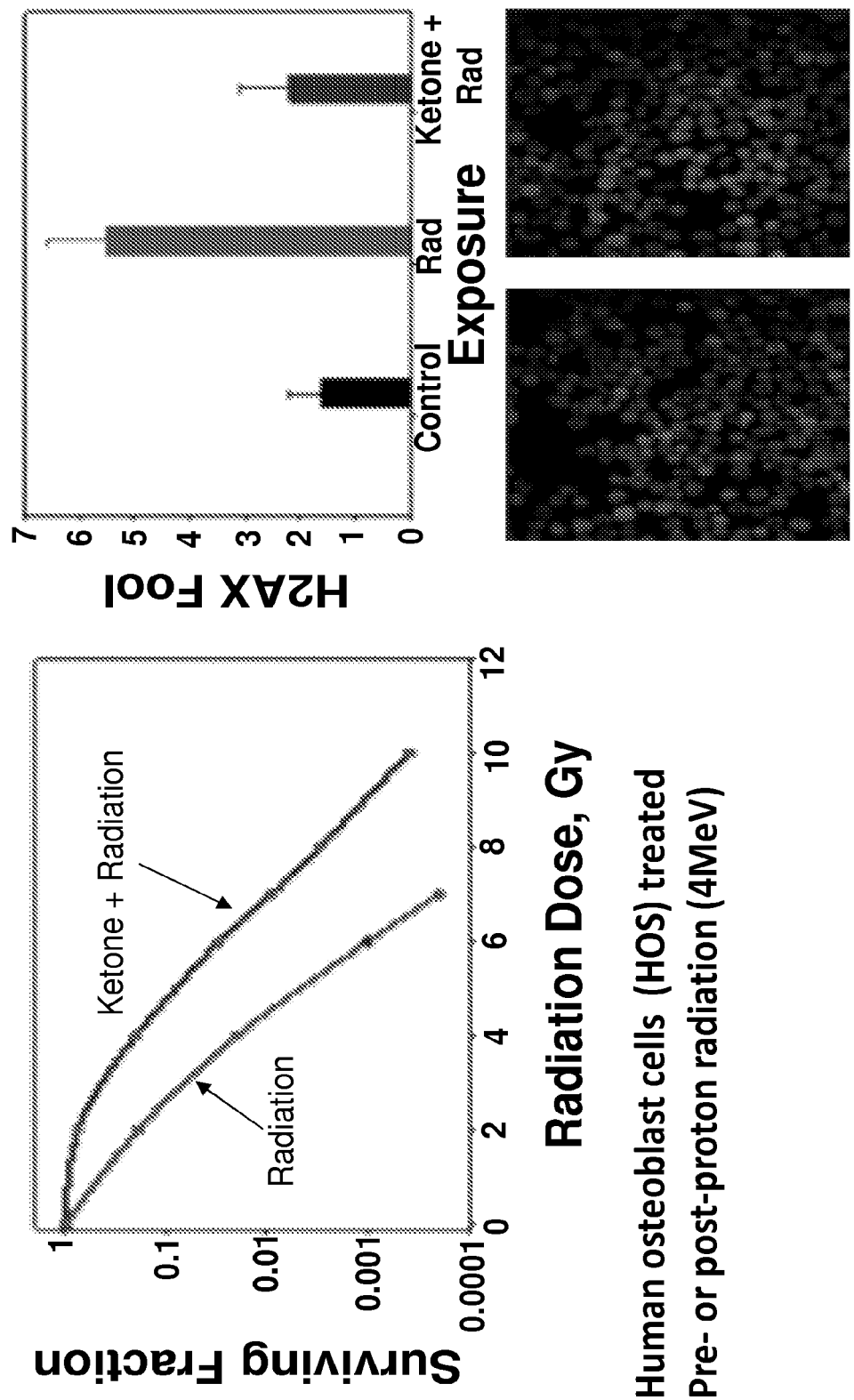
FIG. 3 is a pair of graphs and images illustrating protection against proton radiation after administration of ketones. HOS cells were treated with ketone esters either pre- or post-proton radiation (4 MeV). Ketone treatment prior to proton radiation increased cell survival (left graph) and mitigated DNA damage (right graph).
Figure 4:
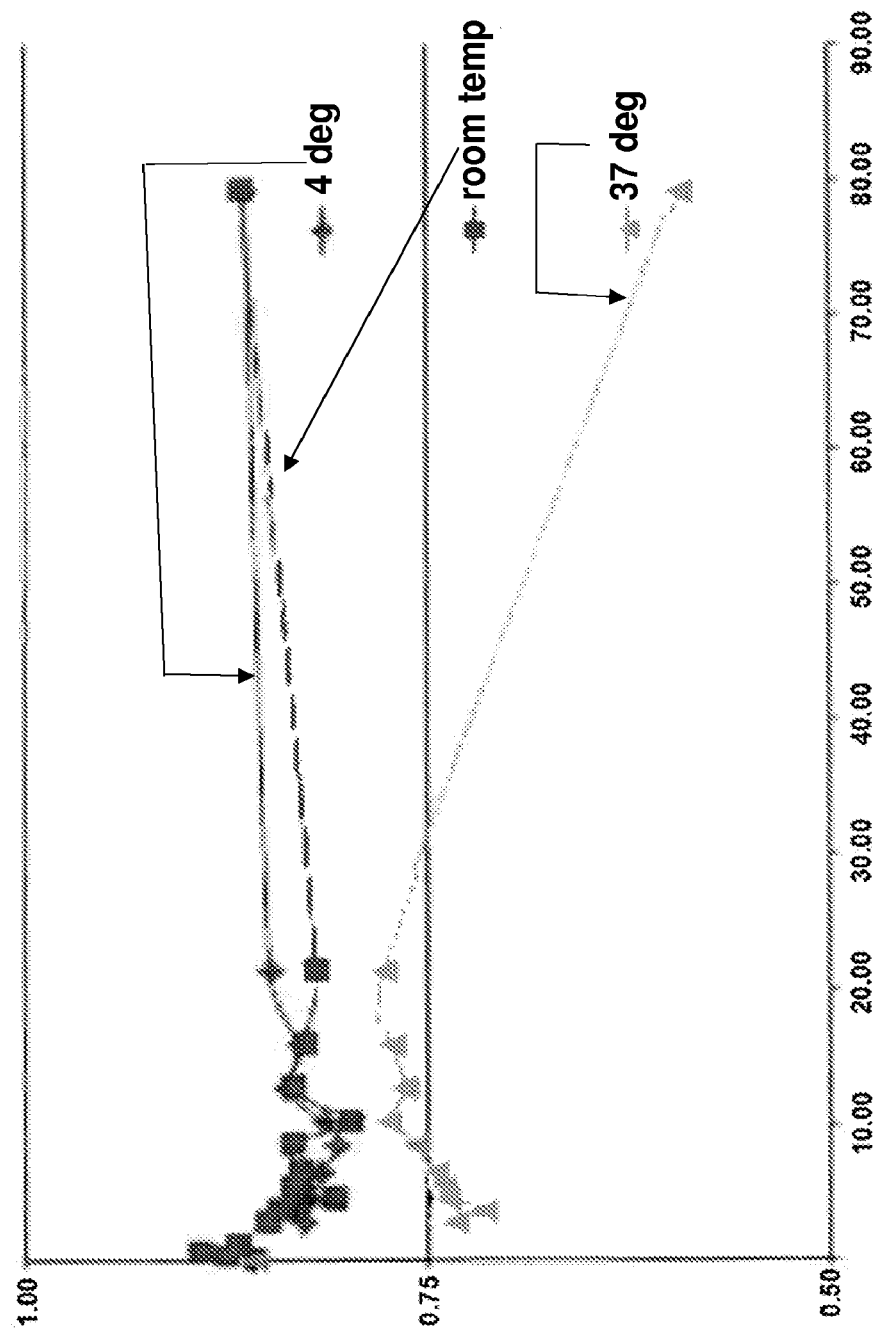
FIG. 4 is a graph illustrating ketone ester stability at pH 7.
Figure 5:
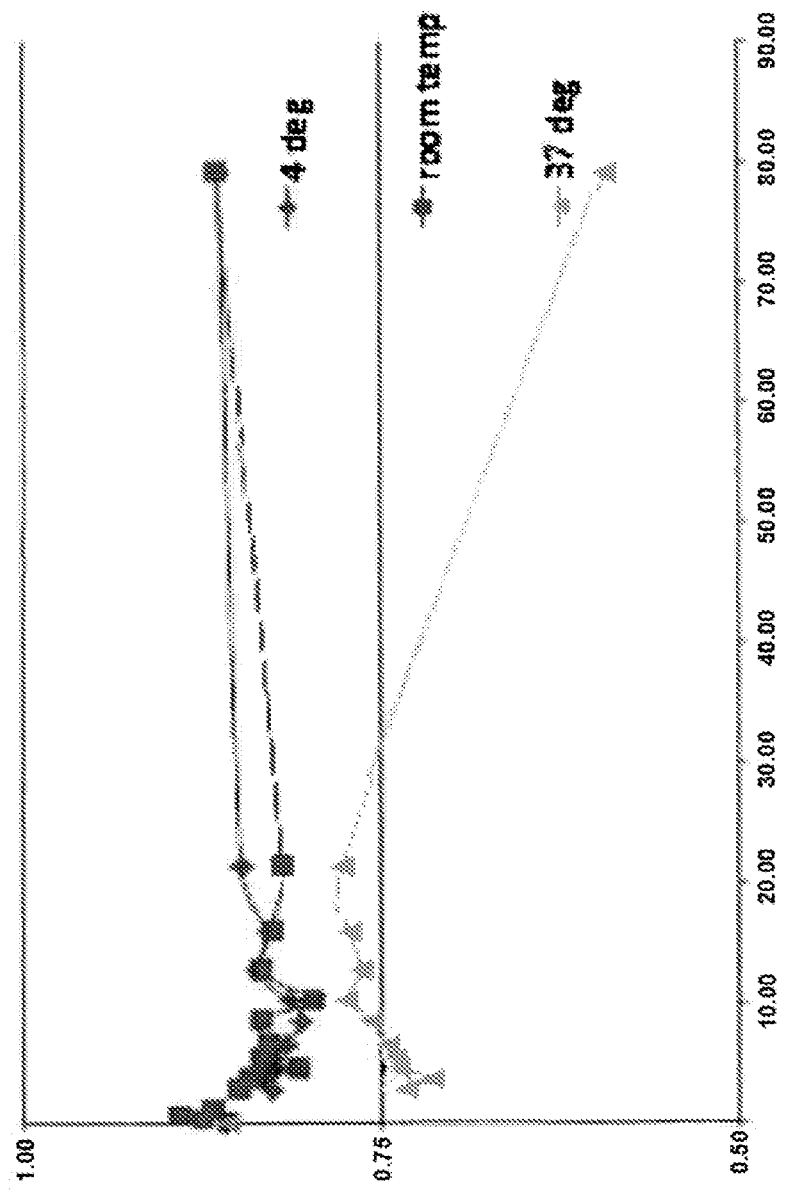
FIG. 5 is a graph illustrating ketone ester blood metabolite levels (5 grams/kg dose, males).

Studies were performed using cultured osteoblasts exposed to gamma radiation with and without (R)-1,3-butanediol ester of (R)-3-hydroxybutyrate as described herein to determine the effect of ketone esters on radiation damage. FIG. 1 is a pair of graphs illustrating cellular radioprotection by ketone esters in which human cultured osteoblast cells were treated pre- or post $^{50}$Co gamma radiation (0.6 Gy/min) with a ketone ester. FIG. 2 illustrates chromosomal protection by ketone esters. FIG. 3 is a pair of graphs illustrating protection against proton radiation after administration of ketones in which human cultured osteoblast cells were treated pre- or post-proton radiation (4 MeV) with a ketone ester. FIG. 4 is a graph illustrating ketone ester stability at pH 7. FIG. 5 is a graph illustrating ketone ester blood metabolite levels. The data presented show that administration of ketone esters after administration of radiation also increases cell salvage. Thus, the present studies indicate that ketones or ketogenic substances administered either before or after exposure to radiation cause dramatic decreases in radiation damage. Without being bound by a particular theory, it is contemplated that metabolism of ketones which increases the cellular content of acetyl CoA, an essential metabolite necessary to accomplish acetylation by histone acetylase enzymes (HAT) may possibly be involved in post-irradiation salvage.

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of these claims.

We claim:

1. A method of protecting animal tissue from damage caused by radiation exposure, comprising contacting the tissue with a therapeutically effective amount of an agent comprising at least one (R)-3-hydroxybutyrate-containing ketogenic material selected from the group consisting of salts of (R)-3-hydroxybutyrate, or esters and oligomers of (R)-3-hydroxybutyrate having a structure selected from the group consisting of:

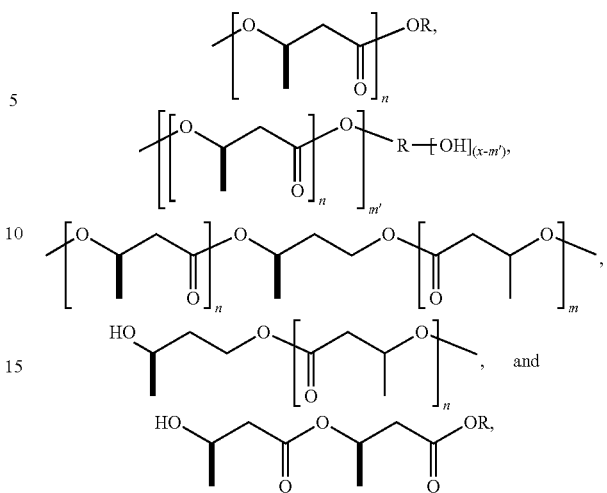

thereby protecting the tissue from radiation damage;
wherein:
n is 1 or more;
R, together with the oxygens to which it is attached, forms an alcohol or alkoxy group;
x is the number of hydroxyl groups attached to R and is selected from the group consisting of 1, 2, 3, 4, 5, 6, and 7;
m' is the number of (R)-3-hydroxybutyrate oligomers attached to R via ester bonds and is less than or equal to x; and
m is 1 or more.

2. The method of claim 1, which is employed as a method of protecting personnel exposed to a radioactive substance or ionizing radiation, comprising contacting tissue of the personnel with the therapeutically effective amount of the said agent.

3. The method of claim 1, wherein contacting is performed at least one of before, during or after exposure to radiation.

4. The method of claim 3, wherein contacting comprises administering to a subject in need thereof the agent within two weeks prior to exposure to radiation, during radiation exposure, and/or within two weeks following radiation exposure.

5. The method of claim 3, wherein contacting comprises administering to a subject in need thereof the agent within two weeks prior to radiation exposure.

6. The method of claim 3, wherein contacting comprises administering to a subject in need thereof the agent within four days prior to radiation exposure, during radiation exposure, and/or within about one day following radiation exposure.

7. The method of claim 1, wherein the radiation comprises an acute or chronic dose of ionizing or non-ionizing radiation.

8. The method of claim 7, wherein the ionizing radiation results from nuclear fission or fusion.

9. The method of claim 7, wherein the ionizing radiation comprises X-rays.

10. The method of claim 7, wherein the ionizing radiation comprises radionuclides.

11. The method of claim 1, which is employed as a method of enhancing the therapeutic window for radiotherapy in a subject, comprising contacting tissue of the subject with the therapeutically effective amount of the said agent prior to the radiotherapy.

12. The method of claim 1 or 11, wherein the radiation exposure comprises diagnostic X-rays, radiation therapy, a CAT-scan, a mammogram, a radionuclide scan, or an interventional radiological procedure under CT or fluoroscopy guidance.

13. The method of claim 1, wherein the radiation exposure comprises tissue-incorporated radionuclides from ingestion of contaminated food or water, non-medical or unintentional exposure to ionizing radiation from a nuclear weapon, non-medical or unintentional exposure to a radioactive spill, cosmic radiation, and/or space flight-associated radiation expose.

14. The method of claim 1, wherein the agent comprises at least one oligomer of (R)-3-hydroxybutyrate.

15. The method of claim 1, wherein the agent comprises at least one ketone ester of (R)-1,3-butanediol according to the formula

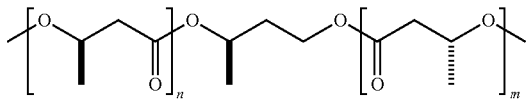

where n and m are 1 or more.

16. The method of claim 1, wherein the agent comprises at least one ketone ester of R-3-hydroxybutyrate according to the formula

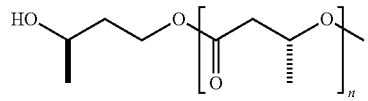

where n is 1 or more.

17. The method of claim 16, wherein n is 3.

18. The method of claim 1, wherein the agent is administered topically, buccally, intraocularly, orally, subcutaneously, intramuscularly, intravenously, intraarterially, transdermally, intranasally, rectally, peritoneally, or by inhalation.

19. The method of claim 1, wherein administering the compound raises the blood ketone body concentration to between 0.1 mM and 20 mM.

20. The method according to claim 19, wherein administering the compound raises the blood ketone body concentration to between 0.2 mM and 10 mM.

21. The method according to claim 19, wherein administering the compound raises the blood ketone body concentration to between 2 mM and 8 mM.

22. The method according to claim 18, wherein administering comprises administering from about 5 grams to about 70 grams of the compound.

23. The method according to claim 18, wherein administering comprises administering from about 70 milligrams to about 5 grams per kilogram of the subject's body weight.

24. The method according to claim 18, wherein administering comprises administering from about 1 gram to about 4 grams per kilogram of the subject's body weight.

25. The method according to claim 18, wherein administering comprises administering 130 grams to about 170 grams per day to the subject.

26. The method of claim 25, wherein administering comprises administering 150 grams per day to the subject.

* * * * *